United States Patent [19]
Klibanov et al.

[11] Patent Number: 5,963,658
[45] Date of Patent: Oct. 5, 1999

[54] METHOD AND APPARATUS FOR DETECTING AN ABNORMALITY WITHIN A HOST MEDIUM

[75] Inventors: Michael Victor Klibanov; Thomas Ramsey Lucas, both of Charlotte, N.C.

[73] Assignee: University of North Carolina, Charlotte, N.C.

[21] Appl. No.: 08/789,632

[22] Filed: Jan. 27, 1997

[51] Int. Cl.$^6$ .................................................... G06K 9/00
[52] U.S. Cl. .......................... 382/128; 382/129; 382/131; 382/132; 382/133; 382/134; 382/252; 382/300; 382/280; 600/310; 600/313; 600/342; 600/407
[58] Field of Search .................................... 382/280, 128, 382/129, 131, 132, 133, 134, 252, 300; 600/310, 313, 314, 342, 407, 476

[56] References Cited

U.S. PATENT DOCUMENTS

| | | | |
|---|---|---|---|
| 3,782,828 | 1/1974 | Alfano et al. | 356/85 |
| 3,811,777 | 5/1974 | Chance | 356/73 |
| 4,850,002 | 7/1989 | Harding et al. | 378/87 |
| 4,972,331 | 11/1990 | Chance | 364/550 |
| 5,062,428 | 11/1991 | Chance | 128/664 |
| 5,070,455 | 12/1991 | Singer et al. | 364/413.19 |
| 5,079,697 | 1/1992 | Chesler | 364/413.2 |

(List continued on next page.)

FOREIGN PATENT DOCUMENTS

| | | |
|---|---|---|
| PCT/US92/00463 | 8/1992 | WIPO . |
| PCT/US92/00464 | 8/1992 | WIPO . |
| PCT/US92/04153 | 11/1992 | WIPO . |
| PCT/US94/02764 | 9/1994 | WIPO . |
| PCT/US94/07984 | 2/1995 | WIPO . |
| PCT/US94/12486 | 5/1995 | WIPO . |
| WO96/32632 | 10/1996 | WIPO . |
| WO97/08538 | 3/1997 | WIPO . |

OTHER PUBLICATIONS

Klibanov, et al., Globally Convergent Numerical Method in Diffusion Tomography, *SPIE Proceedings*, vol. 2570, (1995).

*Mathematics and Physics of Emerging Biomedical Imaging*, Chapters 11 and 14, National Academy Press, Washington D.C., (1996).

(List continued on next page.)

*Primary Examiner*—Leo H. Boudreau
*Assistant Examiner*—Kanji Patel
*Attorney, Agent, or Firm*—Alston & Bird LLP

[57] ABSTRACT

The detection method and apparatus detects abnormalities having a first signal propagation property within a host medium having a second signal propagation property based upon signals which have been reflected, scattered and/or absorbed by the host medium and any abnormalities therein. The detection apparatus includes a signal source for introducing a signal into the host medium which varies with respect to a predetermined signal parameter, such as time, frequency or source location. The detection apparatus also includes a plurality of detectors disposed along some or all of the boundary of the host medium for detecting the signal following propagation through the host medium and any abnormalities within the host medium. The detection apparatus further includes a signal processor for constructing at least one partial differential equation to describe the propagation of a regularized signal through a medium having the same shape as the host medium. The signal processor eliminates at least one term which includes a perturbation function based, at least in part, upon the signal propagation properties of the abnormality. The signal processor can then determine the solution of the at least one partial differential equation and can, in turn, recover the perturbation function. As a result, the detection apparatus can detect abnormalities within the host medium in an accurate, efficient, fast and cost effective manner.

59 Claims, 7 Drawing Sheets

U.S. PATENT DOCUMENTS

| | | | |
|---|---|---|---|
| 5,090,415 | 2/1992 | Yamashita et al. | 128/665 |
| 5,119,815 | 6/1992 | Chance | 128/633 |
| 5,122,974 | 6/1992 | Chance | 364/550 |
| 5,137,355 | 8/1992 | Barbour et al. | 356/342 |
| 5,187,672 | 2/1993 | Chance et al. | 364/550 |
| 5,214,581 | 5/1993 | Rhodes et al. | 364/413.19 |
| 5,274,716 | 12/1993 | Mitsuoka et al. | 382/31 |
| 5,297,033 | 3/1994 | Bito et al. | 364/413.2 |
| 5,327,286 | 7/1994 | Sampsell et al. | 359/561 |
| 5,353,799 | 10/1994 | Chance | 128/664 |
| 5,373,443 | 12/1994 | Lee et al. | 364/420 |
| 5,386,827 | 2/1995 | Chance et al. | 128/633 |
| 5,402,778 | 4/1995 | Chance | 128/633 |
| 5,428,447 | 6/1995 | Toida | 356/372 |
| 5,592,085 | 1/1997 | Ehman | 324/309 |
| 5,694,938 | 12/1997 | Feng et al. | 128/664 |
| 5,713,364 | 2/1998 | Debaryshe et al. | 128/664 |

OTHER PUBLICATIONS

Klibanov, On A Class of Inverse Problems, *Soviet Math. Dokl.*, vol. 26, No. 1, (1982), pp. 248–251.

Buhgeim, et al., Global Uniqueness Of A Class Of Multi-dimensional Inverse Problems, *Soviet Math Dokl.*, vol. 24, No. 2, (1981), pp. 244–247.

Klibanov, et al., On The Solution of Coefficient Inverse Problems By The Method Of Quasi–Inversion, *Soviet Math. Dokl.*, vol. 41, No. 1, (1990), pp. 83–87.

Klibanov, Inverse Problems And Carleman Estimates, *Inverse Problems 8*, (1992), pp. 575–296.

Gutman, et al., Global Convexity In A Single–Source 3–D Inverse Scattering Problem, *IMA Journal of Applied Mathematics*, vol. 55, (1995), pp. 281–302.

Gutman, et al., Two Versions Of Quasi–Newton Method For Multidimensional Inverse Scattering Problem, *Journal of Computational Acoustics*, vol. 1, No. 2, (1993), pp. 197–228.

Klibanov, et al., Consideration Of Solutions To The Inverse Scattering Problem For Biomedical Applications, *SPIE Proceedings*, vol. 1887, (1993), pp. 77–96.

Gutman, et al., Regularized Quasi–Newton Method For Inverse Scattering Problems, *Mathl. Comput. Modeling*, vol. 18, No. 1, (1993), pp. 5–31.

Klibanov, et al., Newton–Kantorovich Method For Three–Dimensional Potential Inverse Scattering Problem And Stability Of The Hyerbolic Cauchy Problem With Time–Dependent Data, *Inverse Problems 7*, (1991), pp. 577–596.

Klibanov, et al., Phaseless Inverse Scattering And The Phase Problem In Optics, *J. Math. Phys.*, vol. 33 (11), (Nov. 1992), pp. 3813–3821.

Klibanov, Numerical Solution Of A Time–Like Cauchy Problem For The Wave Equation, *Mathematical Methods in the Applied Sciences*, vol. 15, (1992), pp. 559–570.

Klibanov, Uniform Strict Convexity Of A Cost Functional For Three–Dimensional Inverse Scattering Problem, *SIAM J. Math. Anal.*, vol. 26, No. 1, (Jan. 1995), pp. 147–179.

Barbour, et al., Mapping Of Photon Distribution And Imaging Of MR–Derived Anatomically Accurate Optical Models Of The Female Breast, *SPIE Proceedings*, vol. 2389, (1995).

Das, et al., Analysis Of Time–Resolved Data For Tomographical Image Reconstruction Of Opaque Phantoms And Finite Absorbers In Diffusive Media, *SPIE Proceedings*, vol. 2389, (1995).

New York State Center for Advanced Technology, Ultrafast Photonic Materials and Applications, The City University of New York, *Release* Dec. 1995.

Strand, Underwater Electro–Optical System For Mine Identification, *SPIE Proceedings*, vol. 2496, (Apr. 1995), pp. 487–493.

Caimi, et al., Underwater Detection Using Coherent Imaging Techniques, *SPIE Proceedings*, vol. 2496, (Apr. 1995), pp. 273–279.

San–Lian Barbour, Randall L. Barbour, Ping C. Koo, Harry L. Graber and Jenghwa Chang, Mapping Of Photon Distribution And Imaging Of MR–Derived Antomically Accurate Optical Models Of The Female Breast, *SPIE*, vol. 2389, 1995, pp. 835–850.

METHOD AND APPARATUS FOR DETECTING AN ABNORMALITY WITHIN A HOST MEDIUM

BACKGROUND OF THE INVENTION

The present invention relates generally to detection methods and apparatus and, more particularly, to methods and apparatus for detecting an abnormality within a host medium.

Imaging systems are widely utilized to construct an image or model of a structure which is otherwise unobservable to the eye. Typically, imaging systems are designed to detect abnormalities, foreign objects or other structures which are embedded within a host medium and which alter or perturb the signal propagation properties of the host medium. For example, x-ray tomography and other medical imaging techniques are commonly used to create an image of a portion of the human body such that tumors or other inclusions can be detected. Similarly, imaging systems have been developed to detect deposits of oil or other minerals within the earth or to detect mines, such as mines buried underground or at sea.

Regardless of the application, conventional imaging systems introduce signals into the host medium and create an image of the host medium and abnormalities within the host medium based upon the interaction of the signals with the host medium and the abnormalities. Typically, an abnormality embedded within a host medium can be identified based upon differences in the signal propagation properties of the host medium and the abnormality. The host medium, as well as any embedded abnormalities, can be defined by a variety of signal propagation properties, such as the diffusion coefficient, the absorption coefficient, the speed of sound, etc. For example, tumors will generally have different signal propagation properties than the surrounding tissue. As a result of these signal propagation properties, the signals introduced by conventional imaging systems into a host medium will be scattered and absorbed in a manner dictated by the respective signal propagation properties of the host medium and any abnormalities within the host medium. Likewise, the signals introduced into a host medium will generally be detected at different times as a result of differences in the relative speed of sound within the host medium and any abnormalities within the host medium.

Conventional imaging systems have typically detected and analyzed the intensity of the signals which had propagated through the host medium in order to create an image of the host medium and any abnormalities within the host medium. Conventional imaging systems have generally treated scattered signals as noise, however, and discarded any information contained by the scattered signals regarding the host medium or any abnormalities within the host medium due to the difficulty of creating an accurate and fast algorithm to describe the behavior of the scattered signals and the excessive computational time required to process the scattered signals by conventional techniques. As used herein, signals which do not propagate along a straight line or along a predefined curve will generally be considered to be scattered.

Although a number of imaging systems are commercially available, these conventional imaging systems do not attempt to provide robust images of the host medium and the abnormalities within the host medium in an efficient, timely and cost-effective manner by the use of scattered signals. One example where the use of scattered signals would be beneficial is during the detection and analysis of cancerous tumors which typically absorb more light than pre-malignant tissues. This is because cancerous tumors are typically of a relatively low absorbing contrast and are thus not readily detectable by x-ray tomography at early stages of development. Another example is provided by imaging systems which discard the scattered signals as noise and rely upon the reflected signals. As a result, these imaging systems have difficulty in detecting abnormalities within a turbid medium since a majority of these signals are scattered and the energy of the unscattered signals, i.e., the ballistic photons, is quite small.

Accordingly, a number of imaging techniques have been developed which collect and evaluate at least a portion of the scattered signals. For example, an article by Barbour, et al., entitled "Mapping of Photon Distribution and Imaging of MR-Derived Anatomically Accurate Optical Models of the Female Breast", SPIE Proceedings, Vol. 2389 (1995) describes an imaging algorithm for creating an image of a breast based upon a previously measured photon distribution. In addition, an article by Das, et al., entitled "Analysis of Time-Resolved Data for Tomographical Image Reconstruction of Opaque Phantoms and Finite Absorbers in Diffusive Media", SPIE Proceedings, Vol. 2389 (1995) describes an imaging system which detects diffusely scattered light and which evaluates the detected light according to another imaging algorithm in order to create an image of the diffusive media. As set forth in these articles, light is introduced from a number of light sources into the test object and the scattered light emerging from the test object is detected. Based upon the detected light, the iterative imaging algorithms described by these articles reconstruct an image of the test object. These iterative algorithms are based on a perturbation model and include a projection onto convex sets algorithm, a conjugate gradient descent algorithm and a simultaneous algebraic reconstruction algorithm.

U.S. Pat. No. 5,070,455 to Jerome R. Singer, et al., also describes an imaging system which generates images of the interior of a test object based upon an analysis of radiation which has been attenuated and scattered by the test object. According to the Singer imaging system, the interior of the test object is modeled as an array of volume elements or voxels. The optical properties of each voxel and, in particular, the scattering and attenuation properties of each voxel are then specified based upon preassigned numerical coefficients.

In operation, the Singer imaging system radiates a test object at a number of points near the exterior of the test object and measures the radiation emerging from the test object at a number of exit points near the exterior of the test object. The imaging system also computes the theoretical intensity of the radiation which would emerge from the test object at each of the exit points if the interior of the test object had the scattering and attenuation properties which are specified for the plurality of voxels. Thereafter, the Singer imaging system determines the difference between the actual intensity of the radiation as measured and the theoretical intensity as computed to determine the magnitude of error therebetween. Based upon a gradient descent methodology, the error function is then minimized by modifying the numerical coefficients representative of the scattering and attenuation properties of each of the voxels. In particular, the numerical coefficients associated with each voxel are iteratively updated until the error function falls below a predetermined threshold value. Based upon the set of numerical coefficients which minimize the error function between the actual intensity and the theoretical intensity, the Singer imaging system generates a series of images of the interior of the test object. See also U.S. Pat. No. 5,137,355 to Randall L. Barbour, et al.

As described above, several imaging systems have been developed to detect and analyze scattered signals in an attempt to overcome the deficiencies associated with conventional imaging systems which discard scattered signals and which rely upon the reflected signals to create an image of the host medium. However, the imaging systems which have been developed to detect and analyze scattered signals, such as those described above, are typically quite computationally intensive and, as a result, may require significant computational time and/or computational resources in order to analyze the scattered signals. For example, the iterative algorithms proposed by the Barbour and Das articles typically require one or more ill-conditioned matrices having many nonzero entries to be solved, thereby significantly increasing the computational time of these imaging systems.

SUMMARY OF THE INVENTION

It is therefore an object of the present invention to provide a new method and apparatus for detecting an abnormality within a host medium, such as for detecting a tumor within the human body.

It is another object of the present invention to provide an apparatus and associated method for detecting an abnormality within a host medium by analyzing scattered signals in a computationally efficient manner.

These and other objects are provided, according to the present invention, by a method and apparatus for detecting an abnormality having a first signal propagation property within a host medium having a second signal propagation property based upon signals which have been both reflected and scattered by the host medium and abnormalities therein. According to the present invention, a signal is introduced into the host medium, such as by a signal source. Preferably, the signal varies with respect to a predetermined signal parameter, such as time, frequency or source location. Following propagation of the signal through at least a portion of the host medium and an abnormality within the host medium, the signal is detected, such as by one or more detectors positioned about the boundary of the host medium. The detected signals, including both scattered and reflected signals, are then analyzed according to the method of the present invention in an accurate, efficient, timely and cost effective manner in order to detect abnormalities within the host medium. As will be apparent, those detection methods and apparatus which detect and analyze scattered signals in a fast and accurate manner will be of most potential practical value.

According to the present invention, at least one differential equation and, more commonly, a coupled system of differential equations is constructed, typically by the constructing means of a signal processor, such as a computer program product. The at least one differential equation is at least partially based upon the propagation of a regularized signal through at least a portion of a medium having the same shape as the host medium. Like the signal introduced by the signal source, the regularized signal also varies with respect to the predetermined signal parameter and space. As a result of abnormalities within the host medium, the differential equation(s) would conventionally include one or more terms which include an unknown perturbation function that is based, at least in part, upon the first signal propagation properties of the abnormality. According to the present invention, however, the differential equation is independent of terms which include the unknown perturbation function. During the constructing of the at least one differential equation, for example, at least one term which includes a perturbation function may be eliminated, typically by the eliminating means of the signal processor. According to the present invention, the solution of the at least one differential equation can then be determined, such as by the determining means of the signal processor, based, at least in part, upon the detected signals.

Even though at least one term which includes the unknown perturbation function is eliminated during the construction of the at least one differential equation, the resulting at least one differential equation describes the propagation of regularized signals through a medium having the same shape as the host medium and including one or more abnormalities. As a result, the at least one differential equation still contains information relating to the abnormalities or, more particularly, the effect of the abnormalities on regularized signals propagating therethrough. Based upon the solution of the at least one differential equation, the method and apparatus of the present invention can recover an approximation of the unknown perturbation function. For example, the signal processor can include recovering means for recovering an approximation of the unknown perturbation function based, at least in part, upon the first signal propagation property of the detected abnormalities. Based upon the approximation of the unknown perturbation function, the detecting means can then detect abnormalities within the host medium.

By constructing differential equation(s) which are independent of terms which include the unknown perturbation function, the computational efficiency of the detection method and apparatus of the present apparatus is significantly improved in comparison with known alternative imaging techniques which detect and analyze scattered radiation. As a result of this new method, the computational time required by the detection method and apparatus of the present invention is significantly reduced.

Based upon the solution of the at least one differential equation, however, the method and apparatus of the present invention recovers an approximation of the perturbation function, including the portion of the perturbation function based upon the first signal propagation property of the abnormalities, and detects abnormalities within the host medium. As a result, the method and apparatus of the present invention can efficiently detect abnormalities and can provide information regarding the signal propagation properties of the abnormalities, thereby potentially identifying the abnormality.

In the various embodiments of the present invention, the signal source can introduce signals which vary according to different predetermined signal parameters. For example, in one embodiment of the present invention, the predetermined signal parameter is time. As a result, the signal source of this embodiment introduces a time-dependent signal into the host medium and the detector detects the signal over time following the propagation of the signal through at least a portion of the host medium. According to this embodiment, the constructing means constructs at least one differential equation at least partially based upon variations in the regularized signal over time and the determining means determines a solution of the at least one differential equation based upon variations in the detected signal over time and space.

In other embodiments, the signal source introduces signals which do not vary in time, but which vary, instead, according to another predetermined signal parameter. According to this embodiment, the signal source introduces a plurality of signals into the host medium which are at least partially defined by the predetermined signal parameter. Preferably, the plurality of signals have different respective values for the predetermined signal parameter which are independent of time. According to this embodiment, the detector detects a plurality of signals corresponding to respective ones of the plurality of signals introduced into the host medium from which abnormalities within the host medium are detected and the signal propagation properties of the abnormalities are recovered.

For example, the predetermined signal parameter can be frequency. According to this embodiment, the signal source introduces a plurality of signals having different respective frequencies into the host medium. Alternatively, the predetermined signal parameter can be the relative location from which the signals are introduced into the host medium. As a result, the signal source of this embodiment preferably introduces a plurality of signals into the host medium from different predetermined locations relative to the host medium. For example, the signal source can be moved along the boundary of the host medium or the signal source can include a plurality of signal sources disposed at different locations about the boundary of the host medium.

In order to further increase the computational efficiency of the detection method and apparatus of the present invention, the signal processor of one advantageous embodiment can include means for approximating the first and second signal propagation properties of the abnormality and the host medium, respectively. In addition, the signal processor of this advantageous embodiment can include means for regularizing the detected signals based upon the anticipated variations in the signals with respect to the predetermined signal parameter following propagation of the signals through a medium having the approximate second signal propagation property and including an abnormality having the approximate first signal propagation property.

In order to more accurately define the first signal propagation property of an abnormality detected within the host medium, the steps of approximating the first and second signal propagation properties, regularizing the detected signal, determining a solution of the differential equation and detecting an abnormality within the host medium are preferably repeated in an iterative manner once the perturbation function has been recovered. In this regard, the approximate first and second signal propagation properties of a subsequent iteration are preferably set equal to the first and second signal propagation properties recovered during a prior iteration of the detection method of the present invention. As a result, the signals detected during the subsequent iteration can be regularized based upon the approximate first and second signal propagation properties recovered during the prior iteration of the detection method.

In one advantageous embodiment, the iterative detection method is continued until the perturbation function recovered during an iteration of the method is less than a threshold value for locations within the host medium. As a result of this iterative process, however, the detection method and apparatus can more accurately determine an approximation of the perturbation function and, in turn, the first signal propagation property of the abnormalities within the host medium.

As described above, the signal processor includes means for analyzing the detected signal to determine variations in the signals with respect to a predetermined signal parameter.

According to one advantageous embodiment, the host medium defines a boundary and the detector includes a plurality of detectors disposed at a plurality of spaced-apart locations along at least a portion of the boundary for detecting signals following propagation of the signals through at least a portion of the host medium. Once the detected signals have been regularized, the analyzing means of this advantageous embodiment can include means for representing the regularized signals associated with each of the plurality of spaced-apart locations by generalized Fourier series having generalized Fourier coefficients. Preferably, the representing means includes means for interpolating between the plurality of generalized Fourier coefficients representative of the regularized signals associated with respective ones of the spaced-apart locations to create a continuous function for each respective generalized Fourier coefficient along at least a portion of the boundary which serves as a boundary condition for the respective generalized Fourier coefficient. As a result, the determining means can determine the solution to the at least one differential equation and, more preferably, the coupled system of differential equations having unknown terms represented by generalized Fourier coefficients based upon boundary conditions imposed by the continuous function for each respective generalized Fourier coefficient.

Accordingly, the detection method and apparatus of the present invention can detect an abnormality within a host medium and can determine the signal propagation properties of the abnormality, such as the diffusion coefficient and the absorption coefficient of the abnormality. By constructing at least one differential equation at least partially based upon the propagation of a regularized signal through at least a portion of a medium having the same shape as the host medium and by eliminating at least one term which includes an unknown perturbation function based, at least in part, upon the first signal propagation property of the abnormality prior to solving the at least one differential equation, the computational time of the detection apparatus and method of the present invention is significantly reduced. According to the present invention, however, an approximation of the perturbation function including the first signal propagation property of the abnormality can be recovered once the at least one differential equation has been solved such that useful information regarding the abnormality can be obtained in an efficient and timely manner.

The computational efficiency of the detection apparatus and method of the present invention is further increased in one embodiment by representing the signals detected along at least a portion of the boundary of the host medium, following regularization, with respective generalized Fourier series having generalized Fourier coefficients. By interpolating between the plurality of generalized Fourier coefficients, a continuous function for each respective generalized Fourier coefficient can be created along at least a portion of the boundary such that the at least one differential equation can be solved in a manner which conforms to the boundary conditions imposed by the continuous function for each respective generalized Fourier coefficient.

DETAILED DESCRIPTION OF THE PREFERRED EMBODIMENTS

The present invention will now be described more fully hereinafter with reference to the accompanying drawings, in which a preferred embodiment of the invention is shown. This invention may, however, be embodied in many different forms and should not be construed as limited to the embodiments set forth herein; rather, this embodiment is provided so that this disclosure will be thorough and complete and will fully convey the scope of the invention to those skilled in the art. Like numbers refer to like elements throughout.

Figure 1:
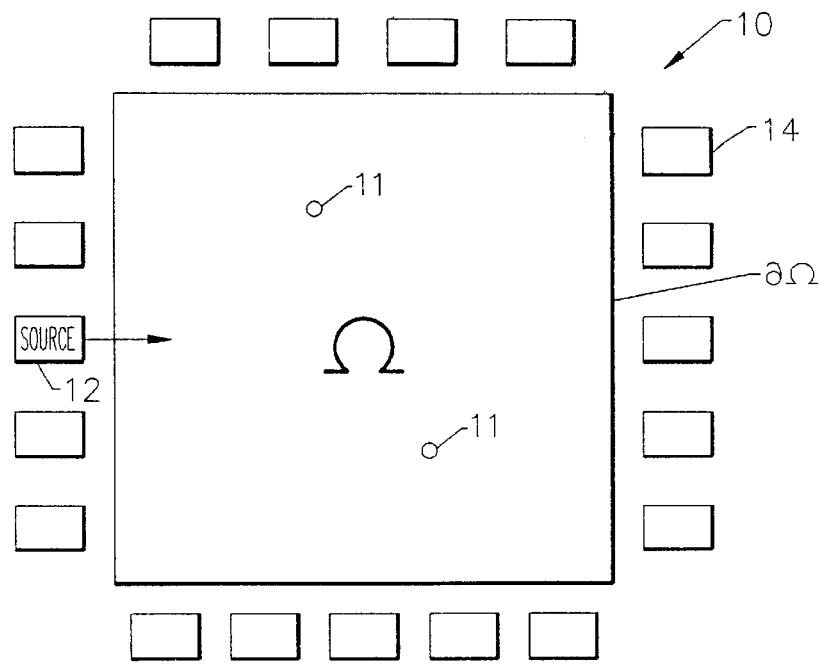
FIG. 1 is a schematic view of a detection method and apparatus according to one embodiment of the present invention in which a plurality of detectors are disposed along the boundary of a host medium.

An apparatus 10 for detecting an abnormality within a host medium $\Omega$ of a predetermined shape according to one embodiment is shown schematically in FIG. 1. While the detection method and apparatus of the present invention will be primarily described in conjunction with the detection of a tumor, the detection method and apparatus of the present invention can also be employed for detecting abnormalities in a number of other host mediums. For example, the detection method and apparatus can be employed to detect mines located underwater or underground. In addition, the detection method and apparatus can detect oil or other mineral deposits which are buried underground. Still further, the detection method and apparatus of the present invention can detect defects hidden within a structure.

As shown in FIG. 1, the detection apparatus 10 includes a signal source 12 for introducing a signal into the host medium. Depending upon the type of host medium, a variety of different types of signal sources can be employed. For example, the signal source can be a source of near infrared light, such as a pulsed laser, for introducing near infrared light into a host medium, such as for the detection of tumors within a breast or another portion of the human body. Likewise, pulsed lasers can introduce optical signals into a host medium, such as turbid water for the detection of underwater mines. Alternatively, other types of signal sources can be employed for introducing other types of signals depending upon the characteristics of the host medium and the abnormality to be detected without departing from the spirit and scope of the present invention. For example, the signal source can be an electromagnetic source or an acoustic source for introducing electromagnetic waves or acoustic waves, respectively, into the host medium.

Regardless of the type of signal source 12, the signal introduced by the signal source is defined by a number of signal parameters, such as time, frequency, amplitude and the position of the signal source relative to the host medium. According to the present invention, the signal source introduces signals into the host medium which vary with respect to at least one of the predetermined signal parameters.

As also shown in FIG. 1, the detection apparatus 10 includes a detector 14 and, more preferably, a plurality of detectors for detecting the signal following propagation through at least a portion of the host medium and any abnormalities within the host medium. As shown in FIG. 1, the host medium generally defines a boundary $\partial\Omega$ along which the detectors are disposed at a plurality of spaced-apart locations. As shown in FIG. 1, the detectors can be disposed about the entire boundary of the host medium. However, the detectors can also be disposed along only a portion of the boundary of the host medium without departing from the spirit and scope of the present invention. For example, in order to detect underwater or underground mines or underground mineral deposits, one or more detectors are generally placed on one side of the mine or mineral deposit, such as on or near the surface of the water or earth in order to detect backscattered signals. In addition, although the detectors are shown to be disposed at a plurality of respective locations which are spaced-apart at equal intervals about the boundary of the host medium, the detectors can be positioned at irregular or unequal intervals about all or a portion of the boundary without departing from the spirit and scope of the present invention.

A number of different types of detectors 14 can be employed without departing from the spirit and scope of the present invention since the type of detector is generally governed, at least in part, by the type of signals introduced by the signal source into the host medium. For example, a detection apparatus 10 which includes a near infrared signal source or an electro-optic signal source 12 can include one or more optical detectors, such as photodetectors, to detect the near infrared or electro-optic signals propagating through the host medium. However, the detection apparatus of the present invention can include a variety of other types of detectors, such as acoustical transducers, without departing from the spirit and scope of the present invention.

As known to those skilled in the art, the signals introduced by the signal source 12 will be absorbed, reflected and scattered by the host medium and abnormalities in the host medium. The manner in which the signals introduced by the signal source propagate through the host medium is typically governed by the signal propagation properties of the host medium as well as the respective signal propagation properties of any abnormalities within the host medium. As known to those skilled in the art, materials, such as the host medium and abnormalities embedded therein, can be defined by a variety of signal propagation properties. For example, a host medium generally has a diffusion coefficient $D(x)$ and an absorption coefficient $a(x)$ which are based, at least in part, upon the scattering cross-section and the absorption cross-section of the host medium, respectively. Likewise, abnormalities within the host medium have signal propagation properties, such as a diffusion coefficient and an absorption coefficient, which are different than the signal propagation properties of the host medium. For example, a cancerous tumor generally has a greater absorbitivity than the surrounding tissue.

Thus, while the abnormality with which the detection method and apparatus 10 of the present invention will be described is a breast tumor and while other examples of abnormalities, such as mines, mineral deposits and structural defects, are provided, the detection method and apparatus of the present invention can detect a wide variety of abnormalities within many types of host mediums so long as the signal propagation properties of the abnormality and the host medium are different. In addition, although the diffusion coefficient D(x) and the absorption coefficient a(x) are particularly advantageous signal propagation properties for use by the embodiment of the detection method and apparatus which models the propagation of signals through the host medium as a diffusion equation, other embodiments of the detection method and apparatus which model the propagation of signals through the host medium in other manners, such as with a wave equation, will utilize other signal propagation properties, such as the relative speed of sound, as described below. As described herein, however, the abnormality will be described as having a first signal propagation property and the host medium will be described as having a second signal propagation property.

Based upon the signals detected by the plurality of detectors 14 positioned about the boundary of the host medium, the detection method and apparatus 10 of the present invention can detect an abnormality within the host medium and can determine the signal propagation properties of the abnormality, thereby aiding in the identification and location of the abnormality within the host medium.

As shown schematically in FIG. 2, the detection apparatus 10 of the present invention preferably includes a signal processor 20, operably connected to the detectors 14, for processing the detected signals as set forth below and for detecting the abnormality. Although the signal processor can be constructed in a variety of fashions as will be apparent to those skilled in the art, the signal processor of one embodiment as well as the various components of the signal processor illustrated in FIG. 2 and described below are comprised of a computer program product. The computer program product includes a computer-readable storage medium having computer-readable program code means, such as a series of computer instructions, embodied in the computer-readable storage medium for processing the detected signals and detecting an abnormality within the host medium.

Figure 2:
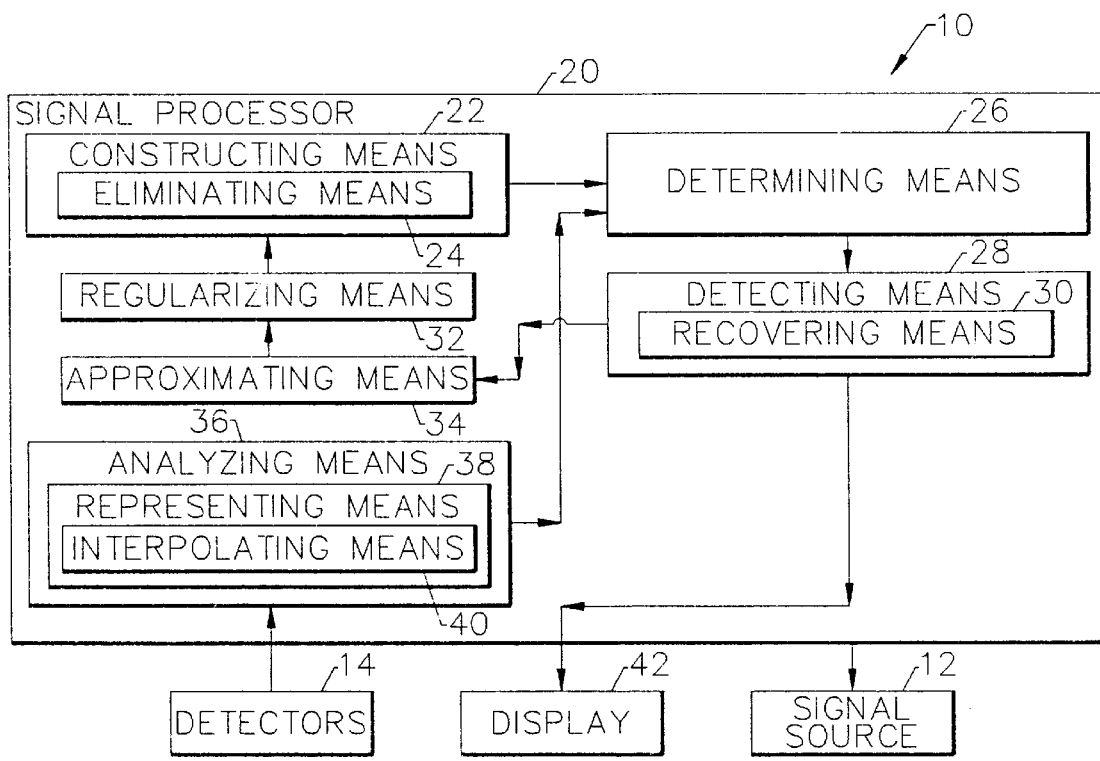
FIG. 2 is a block diagram representing a detection apparatus according to one advantageous embodiment of the present invention.
Figure 6:
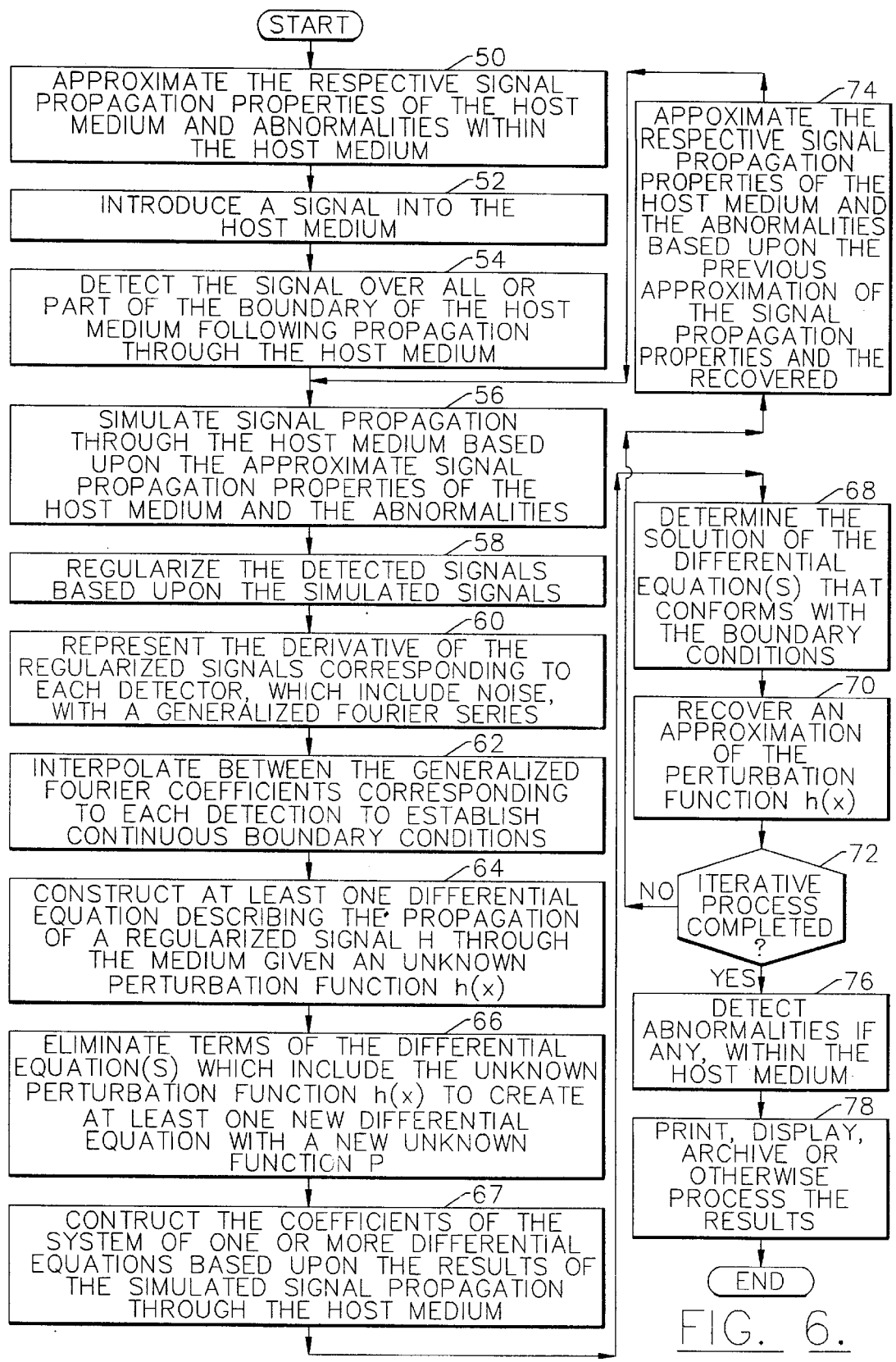
FIG. 6 is a flow chart illustrating the operations of a detection method and apparatus according to one advantageous embodiment of the present invention.

In this regard, FIGS. 2 and 6 are block diagram, flowchart and control flow illustrations of methods, systems and program products according to the invention. It will be understood that each block or step of the block diagram, flowchart and control flow illustrations, and combinations of blocks in the block diagram, flowchart and control flow illustrations, can be implemented by computer program instructions. These computer program instructions may be loaded onto a computer or other programmable apparatus to produce a machine, such that the instructions which execute on the computer or other programmable apparatus create means for implementing the functions specified in the block diagram, flowchart or control flow block(s) or step(s). These computer program instructions may also be stored in a computer-readable memory that can direct a computer or other programmable apparatus to function in a particular manner, such that the instructions stored in the computer-readable memory produce an article of manufacture including instruction means which implement the function specified in the block diagram, flowchart or control flow block(s) or step(s). The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions specified in the block diagram, flowchart or control flow block(s) or step(s).

Accordingly, blocks or steps of the block diagram, flowchart or control flow illustrations support combinations of means for performing the specified functions, combinations of steps for performing the specified functions and program instruction means for performing the specified functions. It will also be understood that each block or step of the block diagram, flowchart or control flow illustrations, and combinations of blocks or steps in the block diagram, flowchart or control flow illustrations, can be implemented by special purpose hardware-based computer systems which perform the specified functions or steps, or combinations of special purpose hardware and computer instructions.

As shown schematically in FIG. 2, the signal processor 20 includes means 22 for constructing at least one differential equation based upon the propagation of a signal through at least a portion of a medium, such as a reference medium, having the same shape as the host medium. Preferably, the at least one differential equation is based, at least in part, upon either the propagation of a regularized signal (as described below) through the reference medium or the derivative (with respect to a predetermined signal parameter) of a regularized signal propagating through the reference medium. As described above, the signals introduced by the signal source 12 are defined by a number of signal parameters, including at least one which varies in a predefined manner. Accordingly, the regularized signal also preferably varies with respect to the predetermined signal parameter and space.

Typically, the constructing means 22 constructs a coupled system of partial differential equations based upon the propagation of the signal, preferably a regularized signal, through a medium having the same shape as the host medium. However, the constructing means can construct different types of differential equations, including different coupled systems of partial differential equations, depending upon the manner in which the propagation of the signal is modeled, as described in detail hereinbelow. For example, the propagation of a signal through the host medium can be modeled by a diffusion equation, a wave partial differential equation or an elliptic partial differential equation without departing from the spirit and scope of the present invention.

As a result of abnormalities within the host medium, the differential equation(s) based upon the propagation of signals therethrough would typically have one or more terms which include one or more unknown perturbation functions (hereinafter collectively referred to as the perturbation function h(x)). The unknown perturbation function h(x) is based, at least in part, upon the first signal propagation properties of the abnormalities. According to the present invention, however, the constructing means 22 constructs differential equations based upon the propagation of signals, such as regularized signals, through a medium having the same shape as the host medium which are independent of terms which include the unknown perturbation function. As described below, the differential equation(s) may, in one alternative embodiment, include a known perturbation function or an approximation or estimate of the perturbation function without departing from the spirit and scope of the present invention. However, the differential equations constructed as described herein do not include any terms which include an unknown perturbation function.

In order to construct at least one differential equation which is independent of terms which include an unknown perturbation function, the constructing means 22 includes means 24 for eliminating at least one term which includes the unknown perturbation function. As set forth in the examples provided below, the perturbation function defines a difference between the anticipated signal propagation properties of the host medium and any abnormalities known to be within the host medium and the actual signal propagation properties of the host medium and abnormalities within the host medium. As such, the perturbation function is based, in whole or in part, upon the first signal propagation properties of the abnormalities within the host medium. By eliminating the terms which include an unknown perturbation function, the solution of the differential equation is greatly facilitated, thereby significantly reducing the computational time of the detection method and apparatus of the present invention. In this regard, it was observed during the development of the present invention that prior imaging systems which detected and analyzed scattered signals generally attempted to detect abnormalities within the host medium by solving for the perturbations introduced by the abnormalities in a direct manner, thereby significantly increasing the computational time of the imaging system.

By way of example, the function $u(x,t)$ can represent the time dependent solution of the differential equation which includes terms involving an unknown perturbation function $h(x)$, while the function $u_0(x,t)$ can represent the solution of the differential equation in instances in which the perturbation function is zero, i.e., no abnormalities are present or the signal propagation properties of the abnormality match the signal propagation properties of the host medium. In order to solve for the unknown perturbation function $h(x)$, the function $v(x,t)$ can be defined as the difference between $u(x,t)$ and $u_0(x,t)$. The equation for the function $v(x,t)$ can not be solved directly, however, since it involves two unknown functions, namely, the function $v(x,t)$ and the perturbation function $h(x)$, which lead to $v(x,t)$ being non-zero. By eliminating the unknown perturbation function $h(x)$, however, the equation for the function $v(x,t)$ can be solved in a greatly simplified manner. By way of example, some of the techniques for eliminating the unknown perturbation function are described below. Thereafter, the detection method and apparatus of the present invention can recover an approximation of the unknown perturbation function $h(x)$, albeit in an indirect manner.

As shown in FIG. 2 and as described in more detail hereinbelow, the signal processor 20 also includes means 26 for determining a solution of the at least one differential equation that is at least partially based upon variations in the detected signal with respect to the predetermined signal parameter. In particular, the signals detected by the detectors 14 along the boundary of the host medium impose boundary conditions upon the at least one differential equation. As a result, the determining means solves the at least one differential equation, following elimination of the unknown perturbation function, in a manner which conforms with the boundary conditions imposed by the detected signals.

Even though the eliminating means 24 has eliminated at least one term of the differential equation that includes the unknown perturbation function, the resulting at least one differential equation describes the propagation of signals through a medium which has the same shape as the host medium and which may include abnormalities in the same relative locations as within the host medium. As a result, the at least one differential equation still contains information relating to the abnormalities or, more particularly, the effect of the abnormalities upon signals propagating through a medium which includes one or more abnormalities.

Figure 3A:
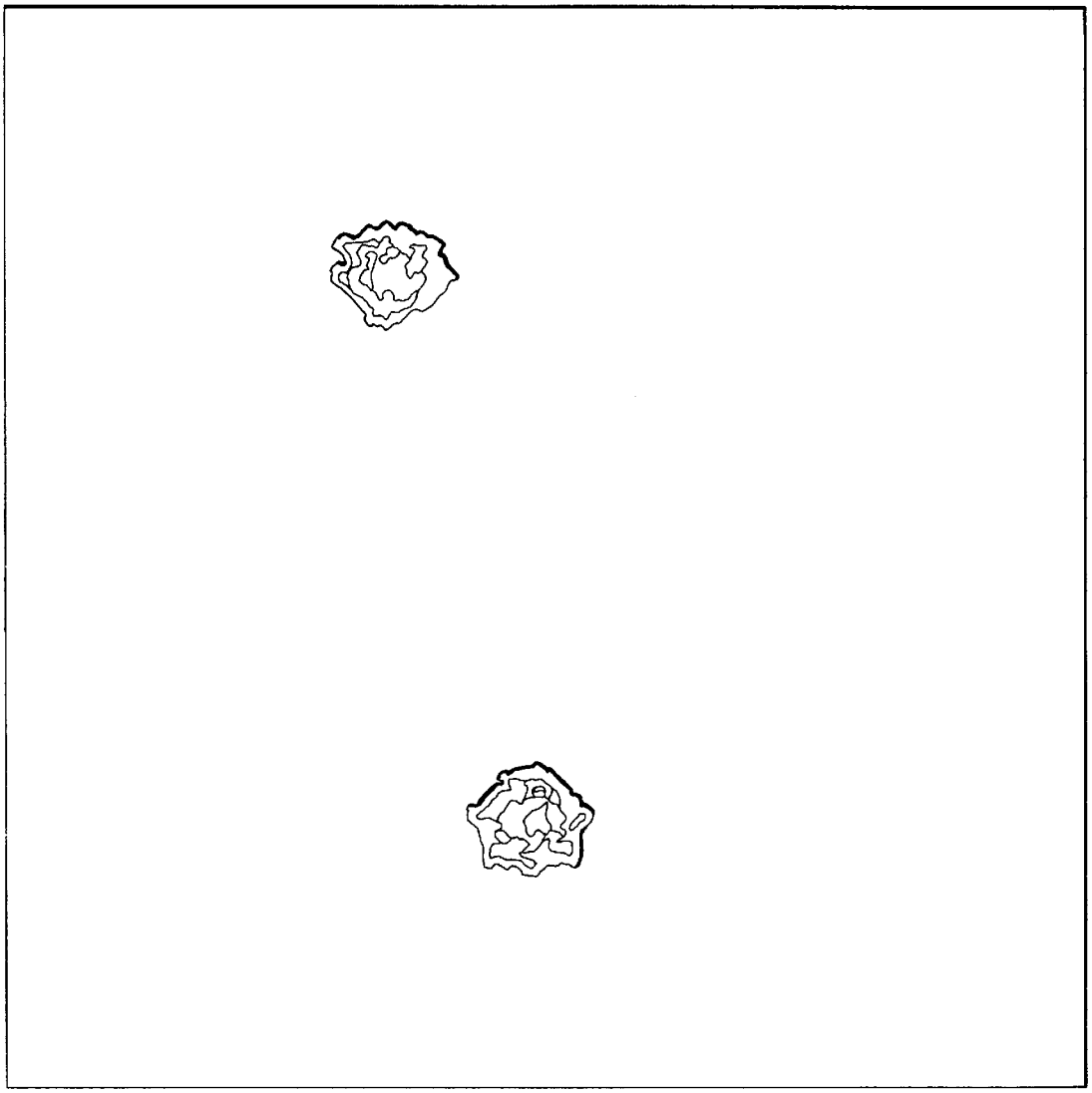
FIGS. 3A and 3B are two-dimensional and three-dimensional images created by a detection method and apparatus according to one advantageous embodiment which illustrate several abnormalities with a host medium.
Figure 3B:
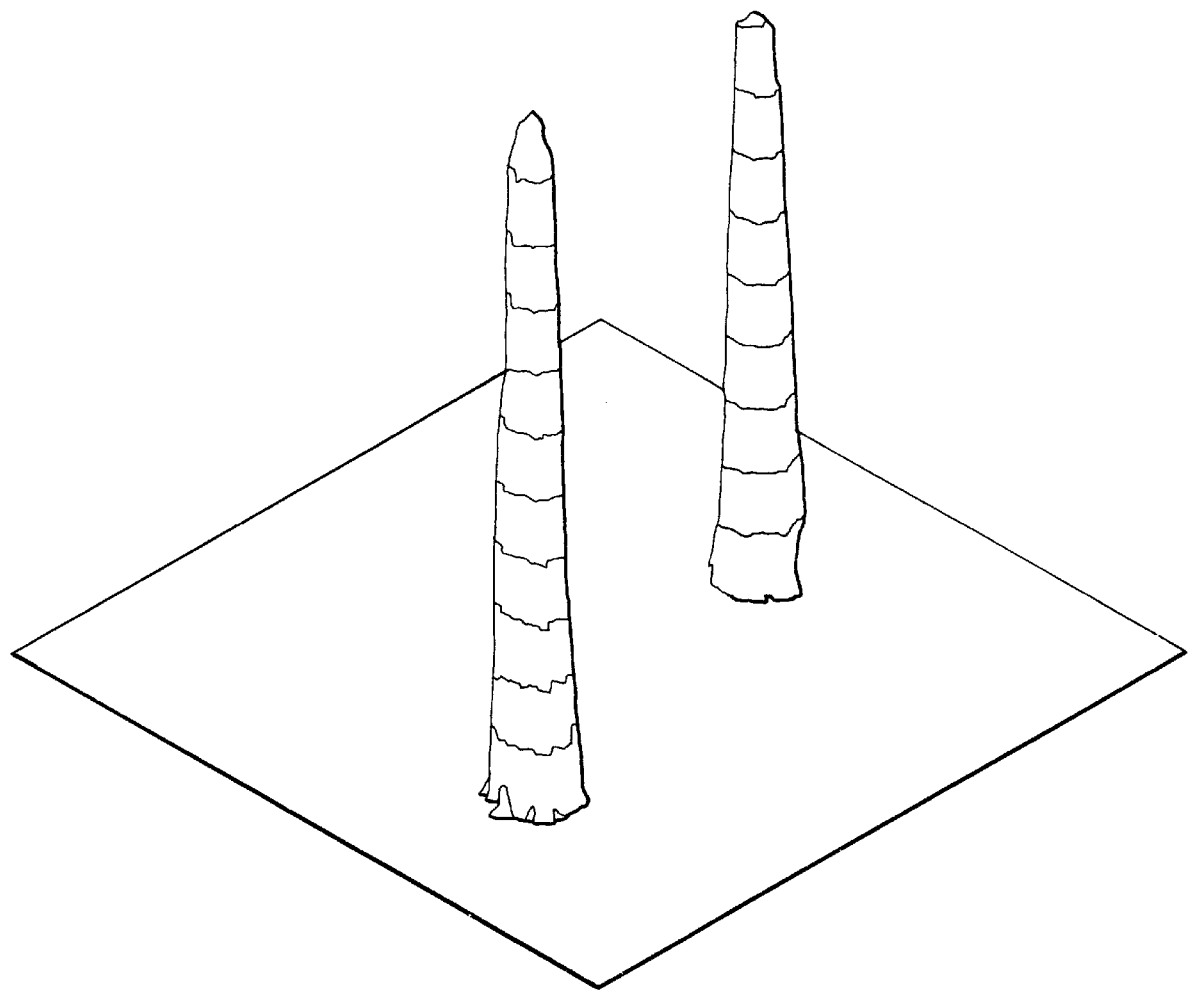

Thus, the signal processor 20 also preferably includes detecting means 28 for detecting an abnormality within the host medium based upon the solution of the at least one differential equation. As described below, the signal processor and, more particular, the detector means not only detects the abnormalities, but also preferably identifies the relative location of the abnormalities within the host medium and creates an image of the abnormalities and the host medium. For example, FIGS. 3A and 3B depict a pair of larger abnormalities as significant deviations from an otherwise uniform host medium.

The detecting means 28 also preferably includes means 30 for recovering an approximation of the unknown perturbation function based upon the solution of the at least one differential equation. By recovering an approximation of the unknown perturbation function, the recovering means can identify any unanticipated differences in the signal propagation properties within the host medium, such as differences in the signal propagation properties within the host medium created by abnormalities within the host medium which have different signal propagation properties than the host medium. By analyzing the approximation of the perturbation function $h(x)$, the presence and location of one or more abnormalities within the host medium. Moreover, the detection method and apparatus 10 of the present invention can aid in the identification of an abnormality by determining the respective signal propagation properties of the abnormality. With respect to medical imaging applications, for example, the detecting means can identify a malignant tumor based upon the signal propagation properties of the tumor, i.e., the increased absorbitivity of the tumor.

Depending upon the type of predetermined signal parameter which varies and the manner in which the propagation of the signal through the host medium is modeled, the signal processor 20 and, more particularly, the constructing means 22 can construct the differential equations in a variety of different manners in order to appropriately describe the propagation of a signal through a medium having the same shape as the host medium. Likewise, depending upon the manner in which the differential equations are constructed, the determining means can solve the differential equations according to a number of different techniques without departing from the spirit and scope of the present invention.

In order to illustrate the detection method and apparatus 10 of the present invention, several advantageous embodiments of the detection method and apparatus of the present invention are described in detail hereinbelow. While the embodiments described in detail below are exemplary of the detection method and apparatus of the present invention, these embodiments are intended to merely illustrate the detection method and apparatus and do not encompass all embodiments of the detection method and apparatus since the detection method and apparatus of the present invention can be implemented in a variety of other fashions as will be apparent to those skilled in the art without departing from the spirit and scope of the present invention.

Figure 4A:
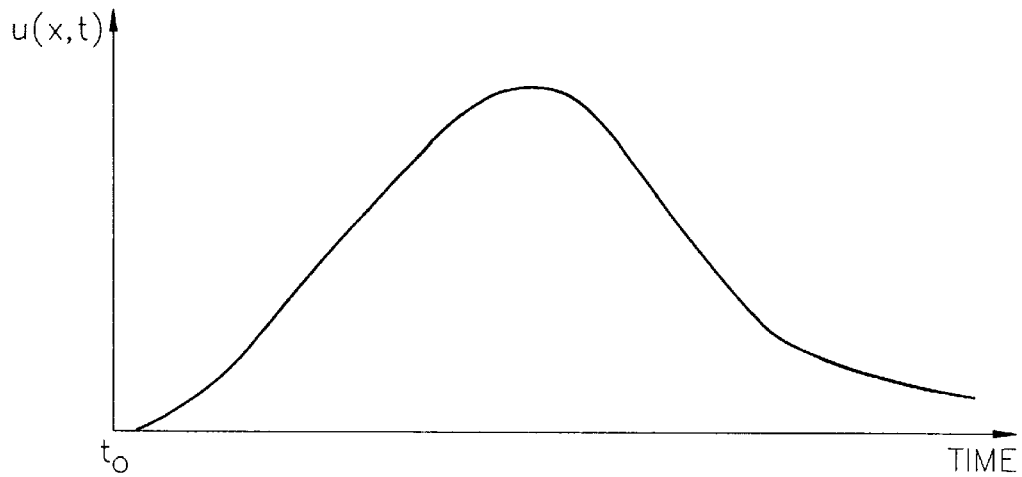
FIGS. 4A, 4B and 4C are graphical representations (drawn to different scales) of the signal amplitude function $u(x,t)$ for photons propagating through a turbid medium, the anticipated or approximate signal amplitude function $u_0(x,t)$ for photons propagating through the turbid medium and the regularized function $H(x,t)+1=u(x,t)/u_0(x,t)$ for a fixed x, respectively.

A. Time Dependent Signal Propagation Modeled by the Diffusion Equation in Which the Diffusion Coefficient $D(x)$ is Known and the Absorption Coefficient $a(x)$ is Subject to Perturbations According to one advantageous embodiment described with reference to FIG. 6, the signal source 12 introduces a time dependent signal into the host medium as shown in block 52. For example, the signal source can be a near infrared source which emits a near infrared pulse into the host medium. The detection apparatus 10 of this advantageous embodiment also preferably includes a plurality of detectors 14 disposed at predetermined locations about the boundary of the host medium, such as the plurality of evenly spaced locations illustrated in FIG. 1. Based upon the near infrared pulse emitted by the signal source, each detector will detect a signal which varies over time following propagation of the signal through at least a portion of the host medium as shown in block 54. For a signal source which emits a signal pulse at a predetermined time $t_{start}$, the detectors will generally detect signals having an intensity profile as shown in FIG. 4A for photons propagating through a turbid medium. As shown, the intensity of the detected signals varies over time as signals which have been reflected and scattered in different manners are received by the detectors. Although the intensity profile at each detector may have the same general shape as shown in FIG. 4A, the respective intensity profile generated by the signals detected at each detector are generally different since the signals detected at each detector have been reflected and scattered in different manners.

While $t_{start}$ can be any predetermined time, $t_{start}$ is typically set to zero in the following examples. In addition, the detector 14 typically only detects signals within a predetermined window of time following the introduction of the signals at time $t_{start}$, such as 1,500 picoseconds to 1,600 picoseconds. Alternatively, the detector can detect signals over the entire period of time during which signals are received, such as 200 picoseconds to 2,000 picoseconds after the introduction of the signals at time $t_{start}$.

In this advantageous embodiment, the predetermined signal parameter is time. That is, the signal source 12 introduces signals which vary with respect to time. As a result, the signal processor 20 and, more particularly, the constructing means 22 will construct at least one differential equation at least partially based upon variations in the signal over time and, more typically, based upon variations in a regularized signal over time, as shown in block 64 of FIG. 6.

As described above, the propagation of a signal through the host medium can be modeled in several different manners, such as a diffusion partial differential equation, a wave partial differential equation or an elliptic partial differential equation. For purposes of illustration, however, the propagation of the signal through the host medium will be initially modeled by the following diffusion equation:

$$u_t(x,t) = div(D(x)\nabla u(x,t)) - a(x)u(x,t) \qquad (1)$$

wherein u(x,t) is the signal amplitude at various times t and at various positions x within the host medium, wherein $u_t(x,t)$ is a partial derivative of the signal amplitude u(x,t) with respect to time, wherein D(x) is the diffusion coefficient of the host medium, wherein a(x) is the absorption coefficient of the host medium, wherein $div(D(x)\nabla u(x,t))$ is the divergence of $(D(x)\nabla u(x,t))$, and wherein $\nabla u(x,t)$ is the gradient operator applied to the function u(x,t). As will be apparent to one skilled in the art, the various positions x within the host medium are vector quantities since the host medium is typically at least two- and, more typically, three-dimensional. For convenience, however, the various positions x will not be represented in vector notation. Instead, it is noted that the variable x generally represents a two- or three-dimensional position vector. As known to those skilled in the art, the signal amplitude u(x,t) also has an initial condition such as is set forth below:

$$u(x,0) = \delta(x - x_0) \qquad (2)$$

wherein $\delta(x-x_0)$ is the impulse response function.

In order to increase the computational efficiency of the detection method and apparatus 10, the signal processor 20 of one advantageous embodiment includes means 32 for regularizing the signal amplitude u(x,t) as shown in blocks 56 and 58 of FIG. 6. That is, a regularized function H(x,t) is constructed as follows:

$$H(x,t) = \frac{u(x,t)}{u_o(x,t)} - 1 \qquad (3)$$

wherein u(x,t) is the actual signal amplitude of the signals following propagation through the host medium and abnormalities disposed within the host medium, and wherein $u_0(x,t)$ is the signal amplitude at a position x and a time t within a reference medium having the same geometrical shape as the host medium, as typically determined by computer simulation. For those skilled in the art, the simulation for $u_0(x,t)$ is known as the forward solver for the partial differential equation set forth in equation 1 with the initial conditions set forth in equation 2 in which the functions a(x) and D(x) are the absorption and diffusion coefficients of the reference medium, respectively. The function u(x,t) is initially known only at the detectors. In addition, a zero boundary condition is typically imposed on the function u(x,t) at the boundary of a slightly larger region than the host medium.

In order to determine $u_0(x,t)$, the signal processor 20 of this advantageous embodiment preferably includes means 34 for approximating the respective signal propagation properties of the host medium and the abnormality. In the present embodiment in which the propagation of a signal is modeled by a diffusion equation, the approximating means can approximate the diffusion coefficient D(x) and the absorption coefficient a(x) of the host medium and any abnormalities known to be in the host medium, as shown generally by block 50. For example, the approximating means can determine the approximate diffusion coefficient and the approximate absorption coefficient based upon numerical or physical estimates of the diffusion coefficient and the absorption coefficient for the particular type of host medium. Alternatively, if the host medium has been examined previously, the approximating means can determine the approximate diffusion coefficient and the approximate absorption coefficient based upon the diffusion coefficient and the absorption coefficient which were determined during the previous examination. For example, for a detection method and apparatus 10 configured to detect breast tumors, the approximating means can equate the approximate diffusion coefficient and the approximate absorption coefficient, at least initially, to the actual values of the diffusion coefficient and the absorption coefficient which were determined during the patient's prior examination, or from typical material properties of female breast tissue, with adjustments for age, using segmented Magnetic Resonance Imaging readings to determine the geometric locations of the various types of breast tissues present.

Figure 4B:
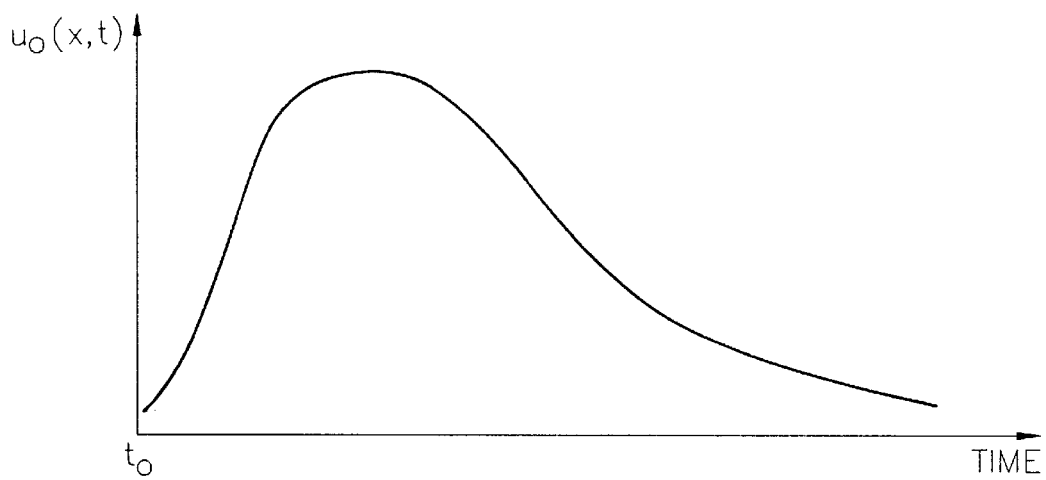
Figure 4C:
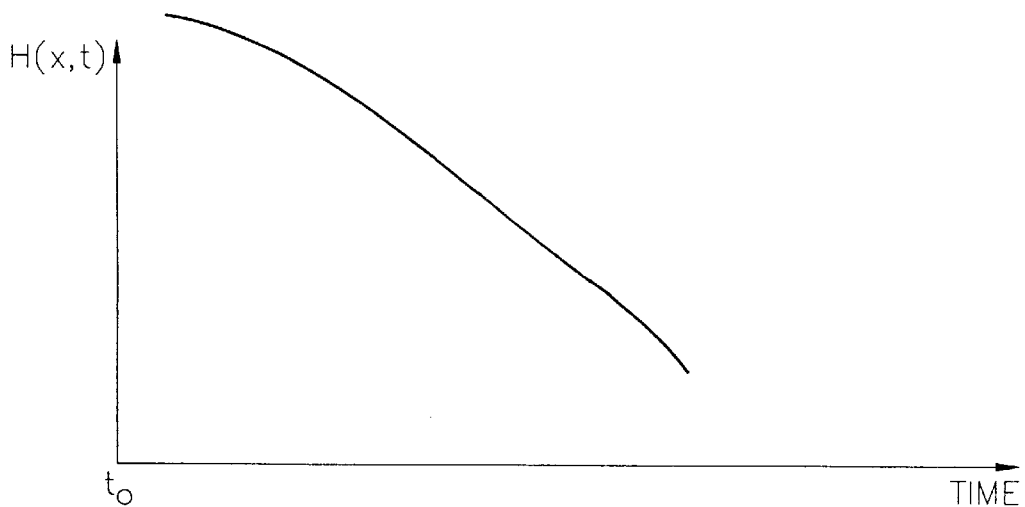

The signal processor can then construct $u_0(x,t)$ to describe the signal amplitude of a signal within a reference medium having the approximate signal propagation properties, such as the approximate diffusion coefficient and the approximate absorption coefficient, of the host medium and any abnormalities known to be within the host medium. One exemplary graphical representation of $u_0(x,t)$ is shown in FIG. 4B. Although both u(x,t) and $u_0(x,t)$ can typically vary significantly, the regularizing means 32 creates a regularized function H(x,t), as shown in FIG. 4C, which varies in a much more systematic manner and can be represented by a polynomial of a lower order, such as a second, third or fourth order polynomial.

More specifically, if the host medium is known to include one or more abnormalities, such as one or more tumors, the approximating means 34 determines not only the approximate signal propagation properties of the host medium, but also the approximate signal propagation properties, such as the approximate diffusion coefficient and the approximate absorption coefficient, of the abnormalities. The signal processor 20 can then construct $u_0(x,t)$ to describe the signal amplitude of a signal within a reference medium having the same shape as the host medium and having the approximate signal propagation properties of the host medium and including one or more abnormalities having the respective approximate signal propagation properties. In instances in which the host medium is not known to include any abnormalities, however, the approximating means need only determine the approximate signal propagation properties of the host medium since there are no known abnormalities and, therefore, no approximate signal propagation properties for the abnormalities.

Based upon the approximate diffusion coefficient $D_0(x)$ and the approximate absorption coefficient $a_0(x)$, the signal amplitude $u_0(x,t)$ within a reference medium can be determined from the following diffusion equation:

$$u_{0t}(x,t) = div(D_0(x)\nabla u_0(x,t)) - a_0(x)u_0(x,t) \quad (4)$$

with suitable boundary conditions, such as $u(x,0)=0$ on the boundary of a larger region than the reference medium, combined with the initial conditions of equation 2. As known to those skilled in the art, this process is referred to as the forward solver.

Figure 7:
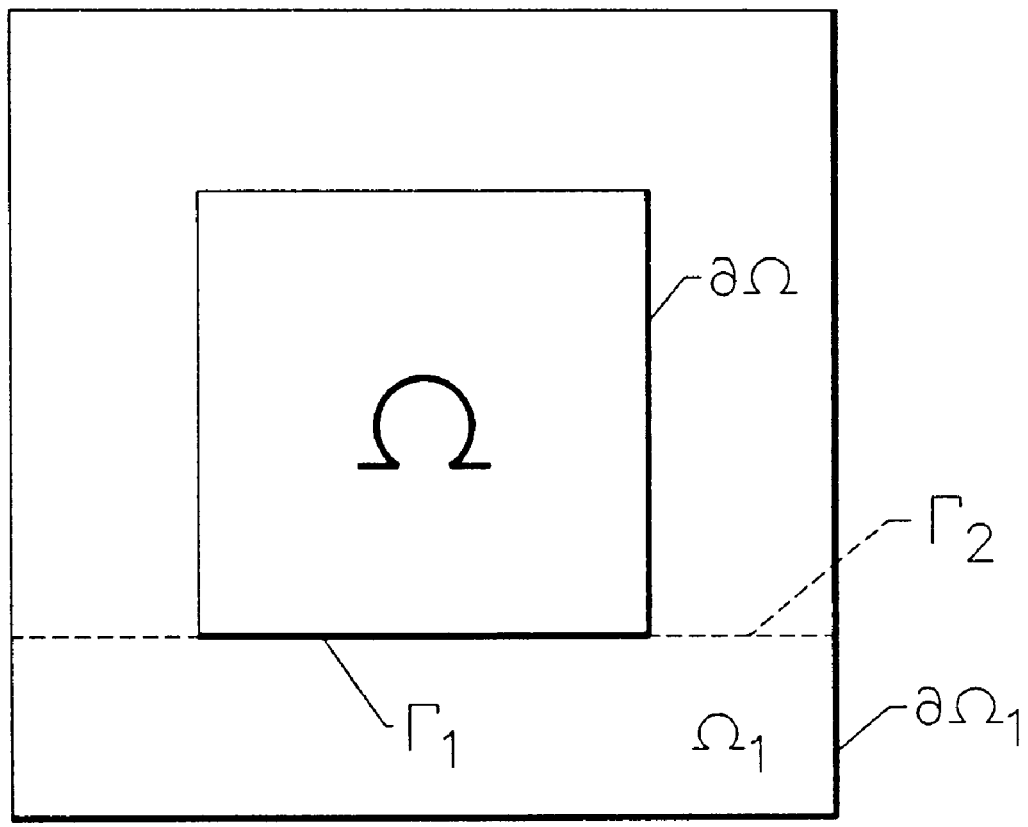
FIG. 7 is a representation of a reference or host medium $\Omega$ in which the abnormalities, if any, are located and a larger domain $\bar{\Omega}$ having known signal propagation properties surrounding the reference or host medium.

By way of illustration, FIG. 7 schematically depicts a reference medium $\Omega$ having a boundary $\partial\Omega$. The reference medium is surrounded by a larger medium $\Omega_1$ defining a boundary $\partial\Omega_1$ at which the boundary condition is imposed. The larger medium has known signal propagation properties which are preferably similar to the signal propagation properties of the host medium. For the analysis of a human breast, for example, the larger medium may have the signal propagation properties of a milk-like suspension. Alternatively, the larger medium may be taken to be a mathematical artifact. In addition, the reference medium is preferably the same size as the host medium, but need not be square as shown in FIG. 7. Instead, the reference medium can be circular or other shapes without departing from the spirit and scope of the present invention.

With respect to the host medium, the actual diffusion coefficient $D(x)$ and the actual absorption coefficient $a(x)$ may be different, at least slightly, from the approximate diffusion coefficient and the approximate absorption coefficient since the signal propagation properties of the host medium may have changed slightly since prior examinations and/or since the host medium may now include one or more abnormalities having different signal propagation properties, i.e., a different diffusion coefficient and a different absorption coefficient, than the host medium.

According to one advantageous embodiment of the present invention, one signal propagation property, such as either the diffusion coefficient or the absorption coefficient, is known or predetermined, while the other coefficient is unknown. In the following description, for example, the diffusion coefficient $D(x)$ will be considered known, while the absorption coefficient $a(x)$ will be considered unknown. However, other embodiments of the detection method and apparatus 10 of the present invention in which the diffusion coefficient $D(x)$ is unknown or in which both the diffusion coefficient and the absorption coefficient are simultaneously unknown will be subsequently described.

Since the actual absorption coefficient $a(x)$ may differ from the approximate absorption coefficient $a_0(x)$ as a result of changes in the host medium or the introduction of one or more abnormalities, the absorption coefficient $a(x)$ can be determined as follows:

$$a(x) = a_0(x) + h(x) \quad (5)$$

wherein $h(x)$ is the perturbation function representing the change or difference between the actual absorption coefficient $a(x)$ and the approximate absorption coefficient $a_0(x)$ including any perturbations in the absorption coefficient caused by abnormalities within the host medium.

Substituting the regularized function $H(x,t)$ and the function $a(x)=a_0(x)+h(x)$ into equation 1 yields the following:

$$H_t(x,t) = div(D(x)\nabla H(x,t)) + \frac{2D(x)}{u_0(x,t)}\nabla u_0(x,t)\nabla H(x,t) - h(x)H(x,t) \quad (6)$$

wherein $H_t(x,t)$ represents the partial derivative of the function $H(x,t)$ with respect to time, and wherein the function $H(x,t)$ satisfies the following initial condition: $H(x,0)=0$. See block 64 of FIG. 6. This initial condition is not trivial, but is one of the key factors of the embodiment of the present invention in which the predetermined signal parameter is time. As subsequently described in conjunction with equation 9, this initial condition permits $H(x,t)$ to be recovered from the derivative of $H(x,t)$. Both $h(x)$ and $H(x,t)$ have relatively small values. As a result, the nonlinear term $|h(x)H(x,t)| << |h(x)|$. According to one advantageous embodiment, the last term of equation 6 can therefore be set to zero to yield the following equation:

$$H_t(x,t) = div(D(x)\nabla H(x,t)) + \frac{2D(x)}{u_0(x,t)}\nabla u_0(x,t)\nabla H(x,t) - h(x) \quad (7)$$

In an alternative embodiment, however, the nonlinear term $h(x)H(x,t)$ of equation 6 could be approximated as an inner iteration, such as by adding the term $-h^{(i-1)}(x)H(x,t)$ or $-h^{(i-1)}(x) H^{(i-1)}(x,t)$ to the right hand side of equation 7. In this regard, i represents the number of the iteration and, as such, takes on successively higher values such as 1, 2 and 3. In addition, $h^{(i-1)}(x)$ and $H^{(i-1)}(x,t)$ are the values of $h(x)$ and $H(x,t)$ found in a previous iteration. As such, this approximation of the nonlinear term $h(x)H(x,t)$ does not include an unknown perturbation function, but, instead, includes a known approximation of the perturbation function. While this discussion of the alternative method includes the full term $-h^{(i-1)}(x)H(x,t)$, other embodiments of the alternative method may only include a fraction of this term, such as $-\sigma h^{(i-1)}(x)H(x,t)$ wherein $0 < \sigma \leq 1$. Even though not described, a similar approach could be employed in other embodiments of the present invention described herein below without departing from the spirit and scope of the present invention.

As set forth above, equation 7 has two unknown functions, namely, $h(x)$ and $H(x,t)$, and is thus difficult to solve in a direct manner. According to the detection method and apparatus 10 of the present invention, the constructing means 22 includes means 24 for eliminating terms which include the unknown perturbation function $h(x)$. See block 66 of FIG. 6. In this example, the eliminating means differentiates equation 7 with respect to time, since $$\frac{\partial h(x)}{\partial t} = 0.$$

By setting $p(x,t)=H_t(x,t)$ and utilizing the initial condition of the function $H(x,0)$, equation 7 can be rewritten as:

$$p_t(x,t) = div(D(x)\nabla p(x,t)) + 2D(x)\frac{\partial}{\partial t}\left[\frac{\nabla u_0(x,t)}{u_0(x,t)}\nabla\left(\int_o^t p(x,\tau)d\tau\right)\right] \quad (8)$$

wherein $p_t(x,t)$ represents the partial derivative of the function $p(x,t)$ with respect to time.

In the alternative embodiment which includes the nonlinear term from the previous iteration, the right hand side of equation 8 would also include the term $-h^{(i-1)}(x)p(x,t)$. In this case, a series of inner iterations or runs would be made beginning with an iteration designated i=1. The term $h^0(x)$ is always zero such that the initial iteration (i=1) of this alternative embodiment employs equations identical to equations 7 and 8. After the recovering means 30 determines the perturbation term $h(x)$, however, this term can be employed during subsequent inner iterations (i=2,3, ...) as $h^{(i-1)}(x)$. In one application of this alternative embodiment, two or three such inner iterations with the additional nonlinear term have been used.

The signal processor 20 then solves equation 8 for $p(x,t)$ such that the function $H(x,t)$ can be recovered as follows:

$$H(x,t) = \int_o^t p(x,t)d\tau \quad (9)$$

According to one embodiment of the detection method and apparatus 10 of the present invention, the signal processor solves equation 8 for the function $p(x,t)$ by approximating the function $p(x,t)$ by a generalized Fourier series having the following form:

$$p_N(x,t) = \sum_{n=1}^{N} a_n(t)Q_n(x) \quad (10)$$

wherein $Q_n(x)$ are the generalized Fourier coefficients, and wherein $a_n(t)$ are Legendre polynomials normalized to a specified time domain, namely, $t_0$ to $t_f$. As a result, these normalized polynomials have the following orthonormality property:

$$\int_{t_0}^{t_f} a_m(t)a_k(t)dt = \begin{cases} 1, & \text{for } m = k \\ 0, & \text{for } m \neq k \end{cases} \quad (11)$$

In this instance, $t_0$ and $t_f$ are beginning and end times, such as 500 picoseconds and 1200 picoseconds, respectively. As will be apparent, $t_0$ and $t_f$ should be selected to be within the entire period of time during which signals are received by the detectors. The beginning and end times and the choice of the number of terms N will vary from one outer iteration to the next. In one exemplary application, however, the number of terms N decreases and the interval size ($t_f-t_0$) is shortened as additional iterations are made.

Accordingly, equation 8 can be rewritten by substituting the generalized Fourier series approximation $p_N(x,t)$ for the function $p(x,t)$ and by multiplying both sides of the equation by $a_k(t)$ to yield the following equation:

$$\sum_{n=1}^{N} a'_n(t)a_k(t)Q_n(x) = \quad (12)$$

$$2a_k(t)D(x)\sum_{n=1}^{N}\frac{\partial}{\partial t}\left(\frac{\nabla u_0(x,t)}{u_0(x,t)}\int_o^t a_n(\tau)d\tau\right)\nabla Q_n(x) +$$

$$\sum_{n=1}^{N} a_n(t)a_k(t)div(D(x)\nabla Q_n(x))$$

In the alternative embodiment which includes the nonlinear term from the previous iteration, the term $$-h^{(i-1)}(x)a_k(t)\sum_{n=1}^{N} a_n(t)Q_n(x)$$

is added to the right hand side of equation 12.

By integrating both sides of equation 8 from $t_0$ to $t_f$, and by relying upon the orthonormality property of the Legendre polynomials as set forth in equation 11, equation 12 can be further simplified to the following coupled system of second order differential equations:

$$div(D(x)\nabla Q_k(x)) + \quad (13)$$

$$2D(x)\sum_{n=1}^{N}\nabla Q_n(x)\int_{t_0}^{t_f} a_k(t)\frac{\partial}{\partial t}\left(\frac{\nabla u_0(x,t)}{u_0(x,t)}\int_o^t a_n(\tau)d\tau\right)dt -$$

$$\sum_{n=1}^{N} Q_n(x)\int_{t_0}^{t_f} a'_n(t)a_k(t)dt = 0, \; 1 \leq k \leq N$$

See block 67 of FIG. 6. In the alternative embodiment which includes the nonlinear term from the previous iteration, the term $-h^{(i-1)}(x)Q_k(x)$ is added to the left hand side of equation 13.

Equation 13 can then be rewritten in a more concise vector form as:

$$A(Q)=0 \quad (14A)$$

wherein the differential operator A is defined by:

$$A(Q)=div(D(x)\nabla Q(x))-[(B_1(x),B_2(x))\cdot\nabla Q(x)]-[C(x)\cdot Q(x)]=0 \quad (14B)$$

wherein $Q(x)$ is a vector valued function and wherein $B_1(x)$, $B_2(x)$ and $C(x)$ are matrix valued functions as set forth below:

$$Q(x) = \begin{pmatrix} Q_1(x) \\ Q_2(x) \\ \vdots \\ Q_N(x) \end{pmatrix} \quad (15)$$

$C(x)=[c_{kn}]$ wherein $$c_{kn} = \int_{t_o}^{t_f} a'_n(t) a_k(t) dt (B_1(x), B_2(x)) =$$

$$\{B_{1kn}, B_{2kn}\} = -2D(x) \int_{t_o}^{t_f} a_k(t) \frac{\partial}{\partial t} \left( \frac{\nabla u_0(x,t)}{u_0(x,t)} \int_o^t a_n(\tau) d\tau \right) dt$$

and A(Q) is the elliptic differential operator defined by equation 14B. In the alternative embodiment which includes the nonlinear term from the previous iteration, the matrix C(x) has the term $h^{(i-1)}(x)$ added to its diagonal elements. Thus, equations 14A and 14B provide both a more concise and computationally clearer form of equation 13.

The signal processor 20 also preferably includes means 26 for determining a solution of the coupled system of partial differential equations. See block 68 of FIG. 6. As shown in block 67 of FIG. 6, the signal processor initially computes the coefficients of the system of coupled differential equations of equation 14. In this regard, the signal processor first runs the forward solver, as described above, to compute the solution of equations 4 and 2, thereby generating a simulated solution $u_0(x,t)$ based upon the current approximation of the absorption coefficient $a_0(x)$ and diffusion coefficient $D_0(x)$. See block 56. Then, the signal processor computes the coefficient matrices $[B_1(x), B_2(x)]$ and C(x) of the operator A defined in equation 14B. Since the forward solver computes the solution at one instant in time after another over a large mesh of spatial points, the terms of the B coefficient matrices can be evaluated by numerical integration in time by adding the results obtained at each new instant in time as the results become available. Thus, the storage or memory required by the signal processor is significantly reduced since storage is required only over a set of spatial points which define the B coefficient matrices, and storage is not required to save the many time values at each spatial point.

The signal processor 20 must also calculate and save the values of either the simulated signal $u_0(x,t)$ or the rate of change of the simulated signal in a direction normal to the boundary of the host medium, i.e., the flux $$\Phi_o(x,t) = \frac{\partial u_o(x,t)}{\partial n},$$

at the various discrete points x on the boundary of the host medium at which the detectors 14 are located. This data can easily be calculated and saved by the signal processor as the above forward solver (block 56) is run, and will be used for the regularization H(x,t). While both embodiments are quite advantageous, the boundary values which are saved by the simulation correspond to the nature of the data collected at the detectors (signal amplitude or flux). While the techniques described below convert measurements of the signal amplitude u(x,t) collected by detectors to the coefficients $Q_n(x,t)$ of a generalized Fourier series for the derivative of the regularized signal H(x,t)=[u(x,t)/$u_0$(x,t)]−1 which form the boundary conditions for the system given by equation 14A, the same technique could alternatively be used for transforming flux to boundary conditions for equation 14A. FIG. 4A shows a sample curve for the signal amplitude u(x,t) for one detector at location x, and the regularized signal H(x,t) is given by FIG. 4C. Note that the time scales of FIG. 4 differ from one figure to another.

The detection method and apparatus 10 of the present invention uses the data calculated and stored by the signal processor 20, as described above, to determine boundary conditions in order to solve the coupled system of second order partial differential equations set forth in equation 14A.

In this regard, the signals detected by the plurality of detectors 14 about the boundary of the host medium combined with the simulated results from a reference medium or from an earlier iteration leads to the establishment of the boundary conditions with which the coupled system of second order differential equations must conform. For the example above, the plurality of detectors can measure the amplitude of the signal over time as shown in FIG. 4A. Thus, at the discrete points about the boundary of the host medium at which the detectors are located, the signal amplitude u(x,t) is known, as identified in block 54 of FIG. 6, and with the saved simulated results $u_0$(x,t) at the same points, the regularized solution H(x,t) of equation 3 can be calculated.

The signal processor 20 also preferably includes means 36 for analyzing the detected signals which, in turn, includes means 38 for representing the function p(x,t) for each detector 14 with a generalized Fourier series from the above values of H(x,t), wherein p(x,t)=$H_t$(x,t). See block 60 of FIG. 6. Thus, the boundary condition imposed by each respective detector can be represented by a generalized Fourier series having N coefficients, such as $Q_1(x)$, $Q_2(x)$, . . . $Q_N(x)$ by fitting p(x,t). While the boundary condition imposed by each detector can be represented by any number of generalized Fourier coefficients, the boundary condition imposed at each detector is represented by two or three generalized Fourier coefficients in one advantageous embodiment.

More specifically, the signal processor 20 first regularizes u(x,t) (see block 54) by use of $u_0$(x,t) (see block 56) to form H(x,t) as defined by equation 3. See block 58. In one exemplary embodiment with a detector at location x, the signal processor then approximates p(x,t)=$H_t$(x,t) by the use of Legendre polynomials orthonormalized over a time range $t_0$ to $t_f$. See equation 11 for the normalization. In this embodiment, p(x,t) is typically in the form of equation 10. Since H(x,t) includes measured data (see block 54), H(x,t) will include some noise which should be removed. One exemplary approach to remove the noise is to first use a larger time interval, $t_{start} < t_{H_0} \leq t_0 < t_f \leq t_{H_f}$, and to begin by smoothing the function H(x,t) over the time interval $[t_{H_0}, t_{H_f}]$ by the use of orthonormalized Legendre polynomials, thereby producing smoothed polynomial functions $H_{smooth}$(x,t) at each detector location x. This approach is the well known least squares method of smoothing. Then, the coefficients $Q_n(x)$ of the generalized Fourier approximations to $p_n(x,t)$ can be determined indirectly using integration by parts as follows:

$$Q_N(x) = \int_{t_o}^{t_f} a_n(t) \frac{\partial H_{smooth}(x,t)}{\partial t} dt = \quad (16)$$

$$a_n(t) H_{smooth}(x,t) \Big|_{t_o}^{t_f} - \int_{t_o}^{t_f} a'_n(t) H_{smooth}(x,t) dt$$

wherein the last integration is computed analytically.

Based on the above, it follows that:

$$p(x,t) \approx p_N(x,t) = \sum_{n=1}^{N} a_n(t) Q_n(x) \quad (17)$$

In an alternative embodiment in which a different approach is taken to determine the coefficient functions $Q_n(x)$ at the detector points x, p(x,t) is approximated indirectly by approximating H(x,t) by integrals of normalized Legendre polynomials. In this embodiment the noisy regularized function H(x,t) is smoothed by the least squares method over the interval $[t_{H_0}, t_{H_f}]$ using the basis functions $\int_0^t a_1(\tau) d\tau, \int_0^t a_2(\tau) d\tau, \ldots, \int_0^t a_n(\tau) d\tau$.

Similar to the previous embodiment, this technique produces a smoother approximation to H(x,t) in the form of:

$$H(x, t) = \sum_{n=1}^{N} \int_o^t a_n(\tau) d\tau Q_n(x) \qquad (18)$$

Subsequently, $$\sum_{n=1}^{N} a_n(t) Q_n(x)$$

is used to approximate p(x,t). Either of the above techniques provides the boundary conditions ($Q_n(x)$, $1 \leq n \leq N$) at the detector points x. See block 60.

While the boundary conditions at each of the detectors are represented by a respective set of generalized Fourier coefficients ($Q_n(x)$, $1 \leq n \leq N$), it is generally desirable to construct boundary conditions about the entire boundary of the host medium, or at least the entire portion of the boundary of the host medium along which the detectors 14 are positioned, such as in instances in which the detectors are only positioned along a portion of the boundary.

Accordingly, the signal processor 20 also preferably includes means 40 for interpolating between the respective generalized Fourier coefficients representing the boundary conditions imposed at each detector position to create a continuous boundary function for each generalized Fourier coefficient. See block 62 of FIG. 6. For example, the interpolating means of this embodiment preferably interpolates between the $Q_1(x)$ values associated with each detector to create a continuous $Q_1(x)$ function about at least a portion of the boundary of the host medium. Likewise, the interpolating means preferably interpolates between the $Q_2(x)$ values associated with each detector such that a continuous $Q_2(x)$ function is created about at least a portion of the boundary of the host medium. This process of interpolation is continued for the remaining $Q_n$ terms, if any, $3 \leq n \leq N$. While a variety of interpolation techniques can be employed without departing from the spirit and scope of the present invention, the interpolating means of one advantageous embodiment utilizes either a linear or a cubic spline interpolation technique.

The signal processor 20 of this advantageous embodiment can then solve the coupled system of second order differential equations (see equation 14), such as by a finite element method or a finite difference method, in conjunction with the boundary conditions. As will be apparent to those skilled in the art, the solution of the coupled system of second order differential equations will create a matrix system representing the generalized Fourier coefficients $Q_1(x)$ $Q_2(x)$, ... $Q_N(x)$ at various points x within the host medium. By substituting these generalized Fourier coefficients into equations 9 and 10, the functions p(x,t) and, in turn by use of equation 9, H(x,t) are determined at a plurality of points within the host medium. Thus, the detection method and apparatus 10 of the present invention can employ a variety of solution techniques without departing from the spirit and scope of the present invention.

As a result of applying standard numerical methods for partial differential equations, the resulting matrix system for Q(x) over a set of mesh points is relatively sparse. As illustrated graphically in FIG. 5, the matrix system for Q(x) has non-zero terms clustered along the diagonal, thereby significantly reducing the computational time of the detection method and apparatus 10 of the present invention since well known solution techniques, such as skyline or band sparse matrix solvers can quickly solve such a well ordered sparse matrix system.

Figure 5:
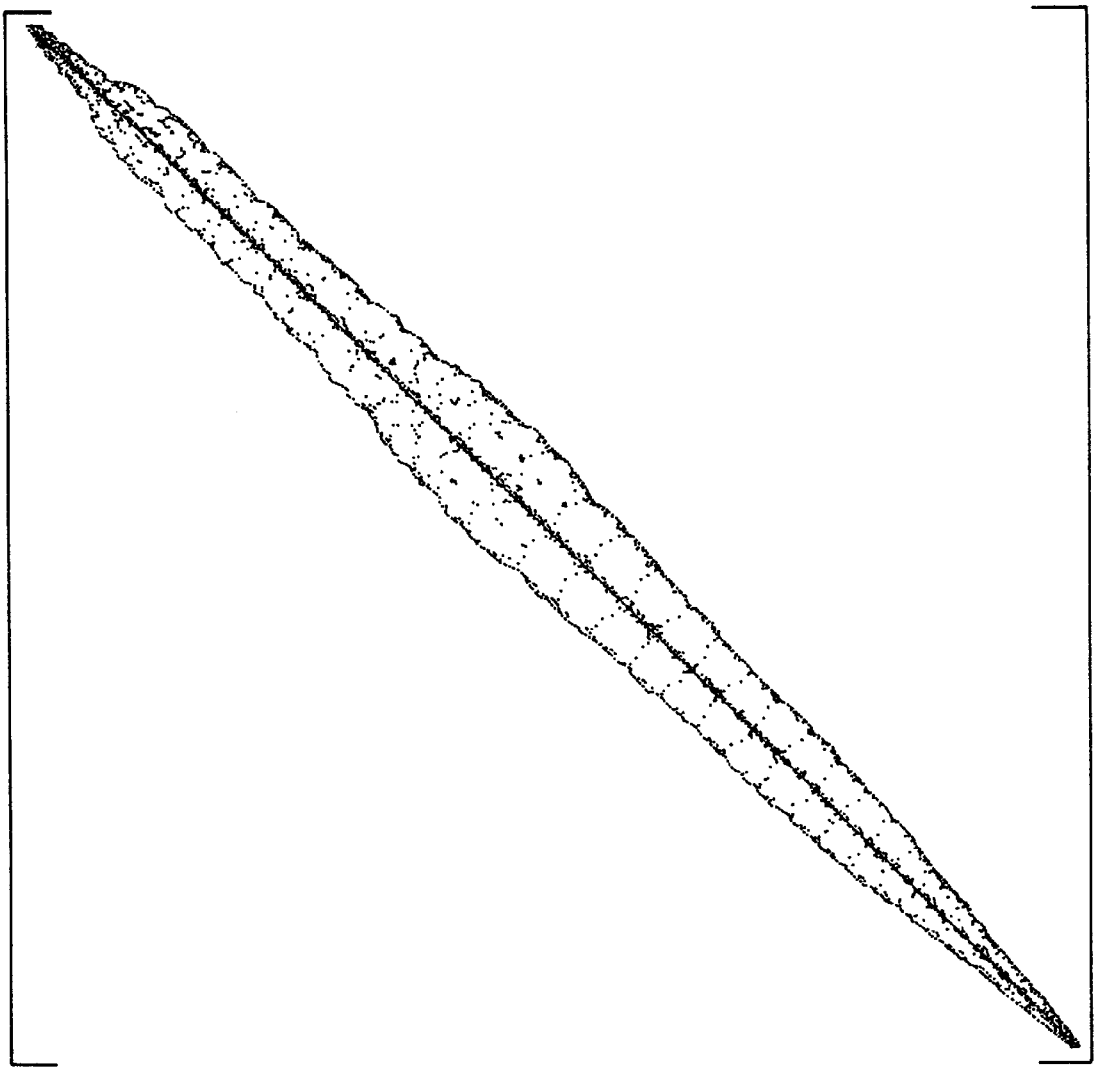
FIG. 5 is a graphical representation of a relatively sparse matrix for $Q(x)$ representing the generalized Fourier coefficients which have coefficients clustered along the diagonal and which is constructed and inverted according to the detection method and apparatus of the present invention.

In marked contrast to the detection method and apparatus 10 of the present invention, it was observed that the conventional imaging techniques which attempted to solve for the perturbations introduced by the abnormalities within the host medium in a direct manner utilized integral equations. As a result of the use of integral equations, however, these conventional imaging techniques typically had to solve dense ill-conditioned matrices having many non-zero entries, such as millions of non-zero entries. The solution of these dense ill-conditioned matrices was significantly more computationally intensive and required significantly more computational time than the solution of a sparse matrix, such as shown in FIG. 5, by the detection method and apparatus of the present invention.

The detection method and apparatus 10 of the present invention also preferably includes means for detecting abnormalities within the host medium based upon the solution of the coupled system of second order partial differential equations. See block 74 of FIG. 6. The detecting means 28 preferably includes means 30 for recovering an approximation of the unknown perturbation function which is based, at least in part, upon the first signal propagation property of the abnormality. See block 70 of FIG. 6. In particular, the recovering means generally recovers an approximation of the unknown perturbation function h(x) which represents the signal propagation properties of abnormalities within the host medium. In one advantageous embodiment, the recovering means determines the signal propagation properties of the abnormality by solving equation 7 for h(x) as follows:

$$h(x) = 2D(x)\frac{\nabla u_o(x, t)}{u_o(x, t)} \nabla H(x, t) + div(D(x)\nabla H(x, t)) - p(x, t) \qquad (19)$$

In the alternative embodiment which includes the unknown term from a prior inner iteration, a term such as $-h^{(i-1)}(x)H(x,t)$ or the variations provided earlier is added to the right hand side of equation 19.

Although h(x), as specified by equation 7, is independent of time, it is to be expected that the computed values of h(x) will vary over time due to the use of the finite generalized Fourier series (set forth in equation 10) and the various approximations employed during the computations. As a result, the signal processor of one advantageous embodiment determines an average value of h(x) with respect to time by integrating equation 19 from $t_0$ to $t_f$ and by dividing the integral by the difference between $t_f$ and $t_0$. It should be apparent, however, that other methods can be employed to solve for h(x) in equation 19 without departing from the spirit and scope of the present invention.

The approximation of the function h(x) obtained by the recovering means 30 of this exemplary embodiment represents a perturbation of the absorption coefficient. This perturbation is generally primarily due to the presence of one or more abnormalities within the host medium. As a result, the function h(x) represents, at least in part, a signal propagation property of the abnormality, namely, the absorption coefficient of the abnormality, at various locations x within the host medium. The function h(x) also represents changes in the absorption coefficient of the host medium from the approximate absorption coefficient.

In order to refine the approximation of the perturbation function h(x), the detection method of the present invention is preferably an iterative process. In particular, the detection method of this advantageous embodiment conducts multiple iterations in which the approximate signal propagation properties are refined based upon the approximation of the perturbation function h(x) recovered by the recovering means 30 during the prior iteration. As shown in block 74 of FIG. 6, for example, during a subsequent iteration, the approximate absorption coefficient of the host medium and any abnormalities disposed therein can be set equal to the approximate absorption coefficient utilized during the prior iteration plus the approximation of the perturbation function h(x) recovered by the recovering means as a result of the prior iteration. By repeating the steps of the detection method as described above with the updated or revised value of the approximate absorption coefficient $a_0(x)$, the detection method and apparatus 10 can then recover another, more refined approximation of the perturbation function h(x). The approximation of the perturbation function h(x) recovered from each successive iteration of the detection method will generally become smaller since the approximate absorption coefficient will approach the actual absorption coefficient of the host medium and any abnormalities within the host medium. Once the approximation of the perturbation function h(x) which is recovered during an iteration meets a stopping criteria, such as by being less than a threshold value, the iterative process of this advantageous embodiment can be halted, as shown in block 72.

As illustrated in block 78 of FIG. 6, the detection method and apparatus 10 of the present invention can then create an image of the signal propagation properties of the host medium and/or any abnormalities detected within the host medium, such as for display upon a video monitor 42, for printing a hard copy or for archival purposes. For example, the detection method and apparatus of this exemplary embodiment can create an image of the abnormalities therein by plotting the last perturbation function h(x) for various points x within the host medium. As a result, the detection method and apparatus can create an image, such as illustrated in FIGS. 3A and 3B, in which abnormalities within the host medium are denoted by the significant differences in the signal propagation properties of the host medium and the embedded abnormalities. The detection method and apparatus can therefore assist in the identification and subsequent treatment of abnormalities based upon the relative location and signal propagation properties of the detected abnormalities.

As described above, the signal processor 20 of one advantageous embodiment can construct and solve the coupled system of second order differential equations by utilizing a single boundary condition based upon the signals detected by the plurality of detectors about the boundary of the host medium. In one alternative advantageous embodiment, a coupled system of fourth order differential equations is solved to produce $Q_1(x), Q_2(x), \ldots Q_n(x)$, which lead to p(x,t), H(x,t) and h(x) as described above. Since fourth order differential equations require two boundary conditions, as contrasted to the single boundary conditions required for the second order system such as given by equation 14A, a second boundary condition must be provided. According to one advantageous embodiment, the second boundary condition, i.e., whichever boundary condition is not provided by the detectors 14, is provided by computer simulation. For example, if detectors 14 measure the signal amplitude u(x,t), the signal processor 20 will approximate the flux $$\frac{\partial u(x,t)}{\partial n}$$

at the detectors by simulation. In particular, the signal processor will run the forward solver, as described above, to solve equation 1 over the region $\Omega_1 \backslash \Omega$, that is, that portion of $\Omega$, which is on or outside of $\Omega_1$. See FIG. 7. In this region, both a(x) and D(x) are known and the value of u(x,t) on $\partial\Omega$ can be approximated from the detected value. However, for points on the exterior boundary $\partial\Omega_1$, u(x,t) is set to 0. The signal processor now runs the forward solver using standard finite element or finite difference methods to solve the diffusion equation (equation 1) with initial conditions as set forth in equation 2 using the above described boundary conditions. From this solution, it is trivial to evaluate $$\frac{\partial u(x,t)}{\partial n}$$

on $\partial\Omega$ for the flux boundary conditions. In the case of simulated solutions, since the solution is known throughout all of $\Omega_1 \backslash \Omega$, the flux and intensity at any point, especially the detector points x, on the boundary $\partial\Omega$ can be easily evaluated and stored by one signal processor.

As described by equation 14B, A(Q) is an elliptic differential operator of the second order. Since both the intensity $\Psi(x,t)$ and the flux $\Phi(x,t)$ can be determined on the boundary $\partial\Omega$ by the above-described techniques, a fourth order elliptic system will be constructed and solved using both boundary conditions. While the detection method has been described heretofore in conjunction with the detection of an abnormality within a plane, the detection method of the present invention can also be applied to three dimensional space. Thus, other embodiments of the detection method are described below for detection in either a plane or in space, corresponding to m being 2 or 3, respectively.

A*(Q), as defined below, is the operator formally adjoint to the operator A(Q):

$$A*(Q) = div(D(x)\nabla Q(x)) + \sum_{j=1}^{m} \frac{\partial}{\partial x_j}(B_j^T(x)Q(x)) - C^T(x)Q(x) \qquad (20)$$

wherein the superscript T indicates the transposition of a matrix. The boundary value problem for the fourth order elliptic system is also defined as follows:

$$(A*A)(Q(x)) = 0, \ Q(x)\bigg|_{\partial\Omega} = \alpha(x), \ \frac{\partial Q(x)}{\partial n}\bigg|_{\partial\Omega} = \beta(x) \qquad (21)$$

If, for example, D(x)=1, then A*A equals $(\nabla^2)^2$ plus terms with derivatives up to the third order. As used here, $(\nabla^2)^2$ is the biharmonic operator defined as follows:

$$(\nabla^2)^2 = \sum_{j=1}^{m} \frac{\partial^2}{\partial x_j^2} \sum_{k=1}^{m} \frac{\partial^2}{\partial x_k^2} \qquad (22)$$

In equation 21, the vector valued functions $\alpha(x)$ and $\beta(x)$ are given boundary conditions. As known by those skilled in the art, these functions can be calculated based upon the given functions $\Psi(x,t)$ and $\Phi(x,t)$ using generalized Fourier decomposition. This Fourier decomposition was previously developed in detail for $\alpha(x)$ in conjunction with the second order system.

The boundary value problem of equation 21 can be solved using the finite element method or the finite difference method. One significant advantage of the finite element method over the finite difference method in solving partial differential equations with coefficients that vary rapidly in isolated regions, however, is the ease with which highly concentrated meshes can be applied in those isolated regions without requiring fine meshes to be applied elsewhere. For fourth order problems, most applications require the use of basis functions that have continuous derivatives, i.e., $C^1$ basis functions, which are difficult to implement, but very powerful. This technique results in a sparse positive definite matrix system. An alternative technique which is easier to implement is the mixed method wherein only the finite element basis functions, and not the derivatives of the finite element basis functions, are required to be continuous ($C^0$ basis functions). The mixed method leads to solving two second order elliptic partial differential equations for every original fourth order partial differential equation. In solving the system of linear algebraic equations resulting from the use of the mixed method with $C^0$ basis functions, a sparse symmetric indefinite matrix system is created.

One exemplary application of the mixed method initially introduces the vector variable w=AQ. Now, the complete system is w−AQ=0 and −A*w=0. After multiplying through by a suitable test function v, and integrating over Ω, as is standard in finite element analysis, the following equations are obtained:

$$\int_\Omega \left( w_i v + D(x)\nabla Q_i(x) \nabla v + \sum_{j=1}^{2} \left( B_j(x) \frac{\partial Q(x)}{\partial x_j} \right)_i v + (C(x)Q(x))_i v \right) dx = \int_{\partial\Omega} D(x) v \frac{\partial Q_i(x)}{\partial n} ds \quad \text{wherein } v \in H^1(\Omega) \tag{23}$$

and $$\int_\Omega \left( D(x) \nabla w_i \nabla v + \sum_{j=1}^{2} (B_j^T(x) w)_i \frac{\partial v}{\partial x_j} + (C^T(x) w)_i v \right) dx = \int_{\partial\Omega} D(x) v \frac{\partial w_i}{\partial n} ds \quad \text{wherein } v \in H_0^1(\Omega) \tag{24}$$

and wherein $1 \leq i \leq N$ and $(\ )_i$ denotes the ith component of the vector valued function contained between the parentheses. In the above example, m was taken to be 2, i.e., the analysis was in a plane, not space. The function space $H^1(\Omega)$ is the set of all functions v defined over Ω such that $v^2$ and the squares of the first derivatives of v have finite integrals over Ω. The function space $H_0^1(\Omega)$ is the subspace of $H^1(\Omega)$ such that v is zero on the boundary of Ω, $\partial\Omega$.

The term $$\int_{\partial\Omega} D(x) v \frac{\partial w_i}{\partial n} ds$$

in equation 24 is zero on $\partial\Omega$ since $v \in H_0^1(\Omega)$ and, thus, is zero on the boundary $\partial\Omega$. To apply the finite element method, nodal $C^0$ quadratic basis functions are applied over a triangular mesh for w, Q and v according to standard techniques known to those skilled in the art, thereby creating a system of 2N×M equations, having M nodes. According to one embodiment, the unknowns are ordered as $w_1^1, Q_1^1, w_2^1, Q_2^1, \ldots w_N^1, Q_N^1, \ldots W_N^M, Q_N^M$. The dependent variables $(w_1^i, Q_1^i, \ldots w_N^i, Q_N^i)$ are all at the node point $(x_i, y_i)$ $1 \leq i \leq M$. Thus, a sparse matrix structure having $M^2$ blocks of size 2N×2N is created which can be viewed as N by N with 2×2 submatrices. Thus, the normal derivative boundary condition of equation 23 is provided by the term $$\int_{\partial\Omega} D(x) v \frac{\partial Q_i(x)}{\partial n} ds = \int_{\partial\Omega} D(x) v \beta_i(x) ds,$$

for $1 \leq i \leq N$, while the boundary condition $Q(x)|_{\partial\Omega} = \alpha(x)$ is an essential boundary condition. As noted above, the functions β(x) and α(x) are the vector boundary conditions as set forth in equation 21. As a result, a symmetric indefinite system of N×N blocks of 2×2 submatrices is created. A typical structure of such a matrix is presented on FIG. 5 in which dots denote non-zero 2×2 submatrices.

The resulting symmetric indefinite matrix system must then be solved. Due to the combination of sparseness, the ordering algorithm, and the underlying positive definiteness of the submatrices related to the mass matrix ($\int$wvdx) and the second order stiffness matrix ($\int$vAQ(x)dx, $\int$vAwdx), the resulting symmetric indefinite matrix system has additional structure. As a result, a symmetric factorization of the form $B = LDL^T$ is typically determined wherein D is a block diagonal matrix consisting of 2×2 submatrices, and L is a matrix with block structure, but with the non-zero blocks clustered about the diagonal as shown in FIG. 5. L has the identity matrix on its diagonal. This approach with pivoting is a standard method to solve the resulting matrix system directly. An advantageous alternative approach is to use an iterative method, such as preconditioned conjugate gradients, modified for symmetric indefinite systems. Both approaches are well known to those skilled in the art.

The direct approach, which maintains the original sparse data structure, has proven quite successful and has led to factorization-solve times for 1024 elements and N=3 of 14 seconds (5 seconds for N=2 and 1.5 seconds for N=1) on a Silicon Graphics Indigo computer with one processor.

B. Time Dependent Signal Propagation Modeled by the Diffusion Equation in Which the Absorption Coefficient a(x) is Known and the Diffusion Coefficient D(x) is Subject to Perturbations In the exemplary embodiment described above, the signal processor 20 modeled the propagation of the signals through the host medium by a diffusion equation in which the diffusion coefficient D(x) is known and the unknown absorption coefficient a(x) is subject to perturbations, such as perturbations introduced by one or more abnormalities. As described above, the detection method and apparatus 10 of this advantageous embodiment can determine the perturbation function h(x) of the absorption coefficient in a precise and efficient manner. In other embodiments in which the signal processor models the propagation of the signals through the host medium with a diffusion equation, however, the absorption coefficient a(x) may be known, but the diffusion coefficient D(x) may be unknown or subject to perturbations, such as perturbations introduced by one or more abnormalities. In these instances, the diffusion coefficient can be represented as $D(x) = D_0(x) + h(x)$ wherein $D_0(x)$ is an approximation of the diffusion coefficient, such as based upon the type of material forming the host medium or based upon a prior evaluation of the host medium. As described above, the function h(x) represents the difference or perturbation between the approximate diffusion coefficient $D_0(x)$ and the actual diffusion coefficient D(x). In addition, the term $\text{div}(D(x)\nabla u(x,t))$ in equation 1 will be approximated by $D(x)\nabla^2 u(x,t)$.

According to this advantageous embodiment in which the signal processor 20 models the propagation of a signal through a host medium according to the diffusion equation, the general diffusion equation set forth in equation 1 can be rewritten as follows:

$$G_t(x,t) = D_0(x)\nabla^2 G(x,t) - a(x)G(x,t) + h(x)\nabla^2 u_0(x,t) + h(x)\nabla^2 G(x,t) \quad (25)$$

wherein $G(x,t) = u(x,t) - u_0(x,t)$ and wherein $G_t(x,t)$ is the partial derivative of the function $G(x,t)$ with respect to time. Since the signal introduced by the signal source 12 is a pulse, the function $G(x,t)$ must meet the initial condition of $G(x,0)=0$. In a similar manner to that described above, the terms $h(x)$ and $G(x,t)$ are relatively small. As a result, the term $|h(x)\nabla^2 G(x,t)|$ is very small and can be set to zero as a first approximation in equation 25. Thus, equation 25 can be rewritten as follows:

$$G_t(x,t) = D_0(x)\nabla^2 G(x,t) - a(x)G(x,t) + h(x)\nabla^2 u_0(x,t) \quad (26)$$

As will be apparent, equation 26 includes two unknown functions, namely, $G(x,t)$ and $h(x)$. In order to reduce the number of unknown functions to one, the signal processor 20 and, more particularly, the eliminating means 24 eliminates terms which include the unknown perturbation function $h(x)$. As described above, the perturbation function $h(x)$ represents perturbations to the diffusion coefficient as a result of changes in the host medium or abnormalities within the host medium. In order to eliminate terms which include the unknown perturbation function $h(x)$, the eliminating means of one exemplary embodiment isolates the function $h(x)$. Since the function $\nabla^2 u_0(x,t)$ could be zero at some values of x and t, however, equation 26 may not be divided by $\nabla^2 u_0(x,t)$ to isolate $h(x)$. In this regard the following functions $G_1(x,t)$ and $\tilde{u}_0(x,t)$ are introduced as follows:

$$G_1(x,t) = \int_0^t G(x,\tau)d\tau$$

$$\tilde{u}_0(x,t) = \frac{1}{D_0(x)}\left[u_0(x,t) + a(x)\int_0^t u_0(x,\tau)d\tau\right] \quad (28)$$

Since $u_0(x,t) > 0$ for $t > 0$, it follows from equation 28 that $\tilde{u}_0(x,t) > 0$ for $t > 0$. In addition, since $a(x) \geq 0$ for $t > 0$, equation 26 can be rewritten as:

$$G_{1t}(x,t) = D_0(x)\nabla^2 G_1(x,t) - a(x)G_1(x,t) + h(x)\tilde{u}_0(x,t) \quad (29)$$

wherein the function $G_{1t}(x,t)$ is the partial derivative of $G_1(x,t)$ with respect to time and wherein the function $G_1(x,t)$ satisfies the initial condition of $G_1(x,0)=0$. By dividing equation 29 by $\tilde{u}_0(x,t)$ and by setting $H(x,t) = G_1(x,t)/\tilde{u}_0(x,t)$, equation 29 can be rewritten as:

$$H_t(x,t) = D_0(x)\nabla^2 H(x,t) + 2\frac{D_0(x)}{\tilde{u}_0(x,t)}\nabla \tilde{u}_0(x,t)\nabla H(x,t) - \\ a(x)H(x,t) - \frac{[\tilde{u}_{0t}(x,t) - D_0(x)\nabla^2 \tilde{u}_0(x,t)]}{\tilde{u}_0(x,t)}H(x,t) + h(x) \quad (30)$$

wherein $H_t(x,t)$ and $u_{0t}(x,t)$ are partial derivatives with respect to time of $H(x,t)$ and $u_0(x,t)$, respectively. Typically, the function $H(x,t)$ satisfies the initial condition of $H(x,0)=0$.

By taking the derivative of equation 30 with respect to time, the eliminating means 24 of this embodiment can eliminate the perturbation function $h(x)$. As a result, the signal processor 20 can solve for the derivative of $H(x,t)$ in a similar manner as set forth above in order to determine the signal propagation properties of the abnormalities, such as the diffusion coefficient of the abnormalities. Based on these signal propagation properties, the signal processor can determine an approximation of the unknown perturbation function and, in turn, can detect abnormalities within the host medium. The detection method and apparatus 10 of this embodiment can also create an image of the signal propagation properties of the host medium and abnormalities detected within the host medium. For example, the detection method and apparatus of this embodiment can create an image of the diffusion coefficient of the host medium and abnormalities therein by plotting the perturbation function $h(x)$ for various points x within the host medium.

C. Time Dependent Signal Propagation Modeled by the Wave Equation

In contrast to the diffusion equation, the signal processor 20 of another embodiment of the present invention can model the propagation of a signal through a host medium with the wave equation as set forth below:

$$u_{tt}(x,t) = c^2(x)\nabla^2 u(x,t) - b(x)u_t(x,t) - a(x)u(x,t) \quad (31)$$

wherein $t \in (0,T)$, wherein $x \in R^n$, wherein $R^n$ represents euclidean space having n-dimensions (n=2 or 3), wherein $u(x,t)$ is the amplitude of a signal wave at a point x at time t, wherein $u_t(x,t)$ and $u_{tt}(x,t)$ are first and second order partial derivatives of $u(x,t)$ with respect to time, respectively, wherein $c(x)$ is the speed of propagation of the signal wave at the point x, wherein $b(x)$ describes the diffusion of signal waves at the point x and wherein $a(x)$ describes the absorption of the signal wave at the point x.

For a detection method and apparatus 10 which utilizes a signal pulse, the wave equation also satisfies the following initial conditions:

$$u(x,0) = 0$$

$$u_t(x,0) = \delta(x - x_0) \quad (32)$$

wherein $\delta(x - x_0)$ is the impulse response function for $x = x_0$.

For signal waves which originate at a point $x_0$, the signal wave will arrive at another point x after a period of time defined by the eikonal function $\tau(x, x_0)$. The eikonal function $\tau(x, x_0)$ satisfies the following eikonal equation:

$$|\nabla_x \tau(x, x_0)|^2 = \frac{1}{c^2(x)} \quad (33)$$

wherein:

$$|\nabla_x \tau(x, x_0)|^2 = \sum_{i=1}^{m} (\tau_{x_i}(x, x_0))^2 \quad (34)$$

wherein m is the dimension of space, i.e., m=2 or 3.

Based upon the eikonal function, $u(x,t)$ can be rewritten as follows:

$$u(x,t) = \delta(t - \tau(x, x_0))\sigma(x, x_0) + \hat{u}(x,t) \quad (35)$$

wherein the function $\hat{u}(x,t) = 0$ for $t < \tau(x, x_0)$ and is smooth for $t \geq \tau(x, x_0)$. In addition, the function $\sigma(x, x_0) > 0$ and depends upon the function $c(x)$ solely.

Two additional functions $w_1(x,t)$ and $w_2(x,t)$ can be defined with respect to $u(x,t)$ as follows:

wherein:

$$w_1(x, t) = \int_o^t u(x, z + \tau(x, x_0)) dz \qquad (36)$$

$$w_2(x, t) = \int_o^t w_1(x, z) dz$$

$$w_1(x, 0) = \sigma(x, x_0) > 0 \qquad (37)$$
$$w_2(x, 0) = 0$$
$$\frac{\partial w_2}{\partial t}(x, 0) = \sigma(x, x_0) > 0$$

By setting $\tau_0(x)=\tau(x,x_0)$, the wave equation set forth in equation 31 can be rewritten as follows:

$$\nabla^2 v(x, t) - 2\nabla v_t(x, t) \cdot \nabla \tau_0(x) - \qquad (38)$$
$$v_t(x, t)\nabla^2 \tau_0(x) - \frac{b(x)}{c^2(x)} v_t(x, t) - \frac{a(x)}{c^2(x)} v(x, t) = 0$$

wherein $v(x,t)$ is either $w_1(x,t)$ or $w_2(x,t)$, and wherein $v_t(x,t)$ is a partial derivative of the function $v(x,t)$ with respect to time.

C1. a(x) Is Unknown, but b(x) And c(x) Are Known

In a like manner to that described above, the detection method and apparatus 10 of this embodiment of the present invention can detect abnormalities within a host medium based upon the signal propagation properties of the abnormalities as defined by the functions a(x), b(x) and c(x). In one advantageous embodiment, the functions b(x) and c(x) are known or predetermined, but the function a(x) is subject to perturbations, such as the perturbations occasioned by one or more abnormalities within the host medium, as set forth above in equation 5. As a result, the function a(x) can be equated to $a_0(x)+h(x)$ wherein $a_0(x)$ is the approximate absorption of a signal wave at the point x and h(x) is the perturbation function representing differences between the actual absorption of a signal wave at point x and the approximate absorption of a signal wave at point x, such as created by errors in estimating the absorbitivity of the host medium or by the introduction of one or more abnormalities within the host medium.

According to this advantageous embodiment, $v(x,t)$ is set equal to $w_1(x,t)$. The approximating means 34 initially sets $a(x)=a_0(x)$ and the signal processor 20 determines the functions $u_0(x,t)$ and $w_{10}(x,t)$ with $a(x)=a_0(x)$. In this regard, equation 38 can be rewritten as follows:

$$v_0(x,t)=w_{10}(x,t)=\int_o^t u_0(x,z+\tau_0(x))dz \qquad (39)$$

In a like manner to that described above, the signal processor 20 of this embodiment can regularize the function $v(x,t)$ as follows:

$$H(x, t) = \frac{v(x, t)}{v_O(x, t)} - 1 \qquad (40)$$

Since the function $\sigma(x,x_0)$ is the same for both $v(x,t)$ and $v_0(x,t)$, the function $H(x,t)$ is subject to the following initial condition:

$$H(x,0)=0 \qquad (41)$$

By substituting the function $v(x,t)=v_0(x,t)[H(x,t)+1]$ into equation 38, the signal processor 20 obtains the following equation:

$$\nabla^2 H(x, t) - 2\nabla H_t(x, t)\nabla \tau_0(x) - H_t(x, t)\nabla^2 \tau_0(x) - \frac{b(x)}{c^2(x)} H_t(x, t) + \qquad (42)$$
$$\frac{2\nabla u_O(x, t)\nabla H(x, t)}{v_O(x, t)} - \frac{2v_{Ot}(x, t)}{v_O(x, t)}\nabla H(x, t)\nabla \tau_0(x) -$$
$$2\frac{\nabla v_O(x, t)\nabla \tau_0(x)}{v_O(x, t)} H_t(x, t) - \frac{h(x)}{c^2(x)} - \frac{h(x)H(x, t)}{c^2(x)} = 0$$

wherein $H(x,0)=0$.

In a like manner as described above, the term $(h(x)H(x,t))/c^2(x)$ is very small and can be set to zero. In addition, the eliminating means 24 can again eliminate the terms which include the unknown perturbation function h(x) by differentiating equation 42 with respect to time.

By then setting $p(x,t)=H_t(x,t)$ and by recognizing that:

$$H(x,t)=\int_o^t p(x,z)dz \qquad (43)$$

equation 42 can be rewritten as:

$$\nabla^2 p(x, t) - 2\nabla p_t(x, t)\nabla \tau_0(x) - p_t(x, t)\nabla^2 \tau_0(x) - \qquad (44)$$
$$\frac{b(x)}{c^2(x)} p_t(x, t) + 2\frac{\partial}{\partial t}\left[\frac{\nabla v_O(x, t)}{v_O(x, t)}\nabla \int_O^t p(x, z)dz\right] -$$
$$2\frac{\partial}{\partial t}\left[\frac{\nabla v_{Ot}(x, t)}{v_{Ot}(x, t)}\nabla \tau_0(x)\nabla \int_O^t p(x, z)dz\right] -$$
$$2\frac{\partial}{\partial t}\left[\frac{\nabla v_O(x, t)\nabla \tau_0(x)}{v_O(x, t)} p(x, t)\right] = 0$$

As described above in conjunction with the solution of the coupled system of partial differential equations which were based upon the diffusion equation, the signal processor 20 of this embodiment can solve the differential equation set forth in equation 44 in a similar manner, such as by employing a finite element or finite difference method. Based upon the solution of the differential equation, the recovering means 30 can recover an approximation of the unknown perturbation function h(x) in the same manner as described above. As also described above, the detection method and apparatus 10 of this embodiment can conduct multiple iterations in order to further refine the approximation of the perturbation function h(x), if so desired.

The approximation of the perturbation function h(x) obtained by the recovering means 30 of this embodiment represents a perturbation of the approximate absorption of a signal wave within the host medium. As described above, this perturbation is generally primarily due to the presence of one or more abnormalities within the host medium. The detection method and apparatus 10 of this embodiment can then also create an image of the signal propagation properties of the host medium and any abnormalities detected within the host medium, such as by plotting the sum of $a_0(x)$ representing the approximate absorption coefficient and the perturbation function h(x) for various points x within the host medium.

C2. b(x) Is Unknown, But a(x) And c(x) Are Known

In the above-described embodiment, the functions b(x) and c(x) of the wave equation were known, but the function a(x) was subject to unknown perturbations. In other embodiments, however, the functions a(x) and c(x) are known, but the function b(x) is unknown and subject to perturbations. As a result, the function b(x) can be represented as $b(x)=b_0(x)+h(x)$ wherein $b_0(x)$ is an approximation of the function b(x) which describes the diffusion of signal waves at point x, and wherein h(x) represents a perturbation to the approximate value $b_0(x)$, such as occasioned by changes in the host medium and/or abnormalities within the host medium. In order to solve equation 38 according to this embodiment, v(x,t) is set equal to $w_2(x,t)$ which leads to the following equation:

$$v_0(x,t)=\int_0^t dy \int_0^y u_0(x,z+\tau_0(x))dz \qquad (45)$$

wherein $v_0(x,t)$ satisfies equation 31 with $b(x)=b_0(x)$, and wherein equation 32 implies:

$$v_{0t}(x,0)=0=\tau(x,x_0)>0 \qquad (46)$$

In order to eliminate the terms which include the unknown perturbation function, the eliminating means 24 isolates the perturbation function $h(x)$. As a result, the signal processor 20 constructs the function $G(x,t)$ as follows:

$$G(x,t)=v(x,t)-v_0(x,t) \qquad (47)$$

By substituting $G(x,t)$ into equation 38, the signal processor 20 obtains the following equation:

$$\nabla^2 G(x,t) - 2\nabla G_t(x,t)\nabla\tau_0(x) - G_t(x,t)\nabla^2\tau_0(x) - \frac{b_0(x)}{c^2(x)}G_t(x,t) - \qquad (48)$$
$$\frac{a(x)}{c^2(x)}G(x,t) - \frac{h(x)}{c^2(x)}v_{0t}(x,t) - \frac{h(x)}{c^2(x)}G_t(x,t) = 0$$

wherein $G_t(x,0)=0$.

In order to linearize equation 48 in a like manner to that described above, the signal processor 20 can set the term $(h(x)G_t(x,t))/c^2(x)$ to zero since this term is very small. The signal processor can then construct the function $H(x,t)$ as follows:

$$H(x,t) = \frac{G(x,t)}{v_{0t}(x,t)} = \frac{v(x,t)-v_0(x,t)}{v_{0t}(x,t)} \qquad (49)$$

wherein if $h(x,t)=0$, then $v(x,t)=v_0(x,t)$ and $H(x,t)=0$. In addition, the function $v_{0t}(x,t)$ represents the partial derivative of $v_0(x,t)$ with respect to time. The signal processor 20 then substitutes $G(x,t)=v_{0t}(x,t)H(x,t)$ into equation 48 to obtain the following equation:

$$\nabla^2 H(x,t) - 2\nabla H_t(x,t)\nabla\tau_0(x) - H_t(x,t)\nabla^2\tau_0(x) + \qquad (50)$$
$$\frac{2\nabla v_{0t}(x,t)}{v_{0t}(x,t)}\nabla H(x,t) - \frac{2\nabla v_{0tt}(x,t)}{v_{0t}(x,t)}\nabla H(x,t)\nabla\tau_0(x) -$$
$$\frac{2\nabla v_{0t}(x,t)\nabla\tau_0(x)}{v_{0t}(x,t)}H_t(x,t) - \frac{h(x)}{c^2(x)} = 0$$

wherein $v_{0tt}(x,t)$ represents the second derivative of $v_0(x,t)$ with respect to time, and wherein equations 46 and 48 and the initial condition $G_t(x,0)=0$ imply $v_{0t}(x,0)\neq 0$ and $H(x,0)=0$.

The signal processor 20 and, more particularly, the eliminating means 24 differentiates equation 50 with respect to time in order to eliminate the unknown perturbation function $h(x)$ which relies, at least in part, upon the signal propagation properties of the abnormality. By setting $p(x,t)=H_t(x,t)$ such that:

$$H(x,t)=\int_0^t p(x,z)dz \qquad (51)$$

equation 50 can be rewritten as follows:

$$\nabla^2 p(x,t) - 2\nabla p_t(x,t)\nabla\tau_0(x) - \qquad (52)$$
$$p_t(x,t)\nabla^2\tau_0(x) + 2\frac{\partial}{\partial t}\left[\frac{\nabla v_{0t}(x,t)}{v_{0t}(x,t)}\nabla\int_0^t p(x,z)dz\right] -$$
$$2\frac{\partial}{\partial t}\left[\frac{\nabla v_{0tt}(x,t)}{v_{0t}(x,t)}\nabla\tau_0(x)\nabla\int_0^t p(x,z)dz\right] -$$
$$2\frac{\partial}{\partial t}\left[\frac{\nabla v_{0t}(x,t)\nabla\tau_0(x)}{v_{0t}(x,t)}p_t(x,t)\right] = 0$$

The signal processor 20 of this embodiment of the present invention can then solve the coupled system of differential equations of equation 52 in a like manner to that described above, such as by employing finite element method or finite difference method. As a result, the detection method and apparatus 10 of this embodiment can detect abnormalities within the host medium by recovering an approximation of the unknown perturbation function $h(x)$ which defines, at least in part, the signal propagation properties of the abnormalities.

C3. $c(x)$ Is Unknown, But $a(x)$ And $b(x)$ Are Known

In still other embodiments in which the propagation of signals through a host medium is modeled by the wave equation of equation 31 and the signal propagation functions $a(x)$ and $b(x)$ are known, but $c(x)$ is unknown and subject to perturbations, the signal processor 20 cannot isolate the function $\tau_0(x)$ since several derivatives of the function $\tau_0(x)$ are included in equation 38. Accordingly, the signal processor must develop a coupled system of differential equations with respect to both functions $p(x,t)$ and $\tau_0(x)$ wherein $p(x,t)$ is associated with $u(x,t)$ in a similar manner to that described above.

In this embodiment of the detection method and apparatus 10, the signal processor 20 sets the function $v(x,t)$ equal to $w_2(x,t)$ such that:

$$v(x,t)=\int_0^t dy \int_0^y u(x,z+\tau_0(x))dz \qquad (53)$$

As a result of equation 37, $v(x,t)$ is subject to the initial conditions of $v(x,0)=0$ and $v_t(x,0)>0$. The signal processor 20 then reformulates equation 38 by substituting $|\nabla_x\tau_0(x)|^2$ for $1/c^2(x)$ and setting $t=0$ to create:

$$v_t(x,0)\nabla^2\tau_0(x)+2\nabla v_t(x,0)\nabla\tau_0(x)+|\nabla\tau_0(x)|^2 b(x)v_t(x,0)=0 \qquad (54)$$

In a like manner to that described above, the approximating means 34 can approximate the eikonal function as $\tau_0(x)$, wherein $\tau_0(x)=\tau(x,x_0)$, based upon the particular type of material of the host medium or based upon the results of a prior evaluation. The signal processor 20 can then represent the eikonal function of this embodiment as $\tau(x)=\tau_0(x)+h(x)$ wherein $h(x)$ represents a perturbation of the approximate eikonal function $\tau_0(x)$, such as based upon changes in the host medium and/or the introduction of abnormalities into the host medium. As a result, the signal processor can construct the function $v_0(x,t)$ as follows:

$$v_0(x,t)=\int_0^t dy \int_0^y u_0(x,z+\tau_0(x))dz \qquad (55)$$

wherein $u_0(x,t)$ is the solution of equations 31 and 32 with $c(x)=c_0(x)$, and wherein:

$$|\nabla_x\tau_0(x)|^2 = \frac{1}{c_0^2(x)} \qquad (56)$$

Finally, the signal processor 20 can determine the relative difference $p(x,t)=v(x,t)-v_0(x,t)$ as follows:

$$\nabla^2 p(x,t) - 2\nabla p_t(x,t)\nabla \tau_0(x) - \tag{57}$$

$$p_t(x,t)\nabla^2 \tau_0(x) - 2(\nabla p_t(x,t)\nabla h(x) + \nabla v_0(x,t)\nabla h(x)) -$$

$$v_{0t}(x,t)\nabla^2 h(x) - p_t(x,t)\nabla^2 h(x) -$$

$$2\nabla \tau_0(x)\nabla h(x)[b(x)(p_t(x,t) + v_{0t}(x,t)) + a(x)(p(x,t) + v_0(x,t))] -$$

$$|\nabla h(x)|^2 [b(x)(p_t(x,t) + v_{0t}(x,t)) + a(x)(p(x,t) + v_0(x,t)] = 0$$

In order to linearize equation 57, the signal processor 20 can set all terms which are products of either h(x) or p(x,t), or the derivatives of h(x) or p(x,t), to zero since all of these terms are quite small. As a result, the signal processor creates the following equation:

$$\nabla^2 p(x,t) - 2\nabla p_t(x,t)\nabla \tau_0(x) - \nabla^2 \tau_0(x)_0 \nabla p_t(x,t) - \tag{58}$$

$$(\nabla \tau_0(x))^2 (b(x)p_t(x,t) + a(x)p(x,t)) - 2\nabla v_0(x,t)\nabla h(x) -$$

$$2(b(x)v_{0t}(x,t) + a(x)v_0(x,t))\nabla \tau_0(x)\nabla h(x) - v_{0t}(x,t)\nabla^2 h(x) = 0$$

which can be rewritten for t=0 as:

$$\nabla^2 h(x) + \frac{\nabla^2 \tau_0(x)}{v_{0t}(x,0)} p(x,0) + 2\frac{\nabla v_{0t}(x,0)}{v_{0t}(x,0)} \nabla h(x) + \tag{59}$$

$$2\frac{\nabla \tau_0(x)\nabla p_t(x,0)}{v_{0t}(x,0)} + \frac{b(x)|\nabla \tau_0(x)|^2}{v_{0t}(x,0)} p_t(x,0) = 0$$

The signal processor 20 then solves equation 59 for the expression $\nabla^2 h(x)$ and substitutes this expression for $\nabla^2 h(x)$ into equation 58 to obtain the following equation:

$$\nabla^2 p(x,t) - 2\nabla \tau_0(x)\nabla p_t(x,t) - \tag{60}$$

$$\nabla^2 \tau_0(x)p_t(x,t) - |\nabla \tau_0(x)|^2 (b(x)p_t(x,t) + a(x)p(x,t)) -$$

$$2\nabla v_0(x,t)\nabla h(x) - 2(b(x)v_{0t}(x,t) + a(x)v_0(x,t))\nabla \tau_0(x)$$

$$\nabla h(x) + [\nabla^2 \tau_0(x)p_t(x,0) + 2\nabla v_{0t}(x,0)\nabla h(x) +$$

$$2\nabla \tau_0(x)\nabla p_t(x,0) + b(x)|\nabla \tau_0(x)|^2 p_t(x,0)]\frac{v_{0t}(x,t)}{v_{0t}(x,0)} = 0$$

The signal processor 20 can now simultaneously solve equations 59 and 60 in a similar manner to that described above in which the function p(x,t) is represented as a finite generalized Fourier series having N+1 coefficients, namely, $Q_1(x), \ldots Q_{N+1}(x), Q_{N+1}(x)$. In this embodiment, the perturbation function h(x) can be regarded as the unknown function $Q_{N+1}(x)$. By simultaneously solving the system of equations set forth in equations 59 and 60 with respect to the generalized Fourier coefficients of p(x,t), the signal processor can solve for the function p(x,t) such that the solution conforms with the boundary conditions imposed by the signals detected at the boundary $\partial\Omega$ of the host medium $\Omega$, namely, $\tau(x)=r(x)$ for $x\in\partial\Omega$ and $$\frac{\partial \tau(x)}{\partial n} = k(x)$$

for $x\in\partial\Omega$, wherein r(x) and k(x) are the signal amplitude and the flux, respectively, detected by the plurality of detectors 14. For example, the signal processor can solve for the functions p(x,t) and, in turn, h(x) by means of the finite element or finite difference method as known to those skilled in the art.

In the above examples, the signal introduced by the signal source 12 varies with respect to time. As a result, the predetermined signal parameter was time and the eliminating means 24 of the signal processor 20 eliminated the perturbation function h(x) by differentiating a corresponding partial differential equation with respect to time since the perturbation function h(x) did not vary as a function of time.

D. Non-time Dependent Signals

According to the present invention, however, the signal source 12 may introduce signals which vary according to predetermined signal parameters other than time. For example, the signal source can introduce signals which vary in frequency, including modulated signals which vary in modulation frequency. Alternatively, the position at which the signals are introduced relative to the host medium can be varied. In either instance, however, the detectors 14 detect a signal corresponding to each of the different signals introduced by the signal source. For example, the detectors would detect the signals corresponding to the signals introduced at each of the different frequencies or from each of the different source locations.

In one model, the signal propagation properties of the host medium and the abnormalities within the host medium are assumed to vary very little or not at all with respect to either the frequency of the signals (in the embodiment in which the signal propagation property is frequency) or the relative location at which the signals are introduced into the host medium (in the embodiment in which the signal propagation property is the source location). As a result, the eliminating means 24 of the signal processor 20 can eliminate the unknown perturbation function in a like manner to that described above by differentiating the partial differential equation with respect to the predetermined signal parameter, such as frequency or source location.

E. Source Position Dependent Signal Propagation Modeled by the Diffusion Equation Although the detection method and apparatus 10 of the present invention has been described in great detail in the context of a time dependent signal, the detection method and apparatus of the present invention will now be described in the context of a signal which is introduced at various locations $x_0$ relative to the host medium. Preferably, the signals introduced at each of the locations have the same frequency k and, according to one advantageous embodiment, are DC signals such that k=0.

As described above, the propagation of a signal through a host medium can be described according to the diffusion equation as set forth in equation 1. In addition, the signal amplitude function u(x,t) can be transformed via a Fourier transformation as follows:

$$v(x,x_0,k) = \int_0^\infty e^{-ikt} u(x,t) dt \tag{61}$$

By assuming that both the diffusion coefficient D(x) and the signal amplitude function u(x,t) change slowly within the host medium $\Omega$, the term $\text{div}(D(x)\nabla u(x,t))$ can be approximated by $D(x)\nabla^2 u(x,t)$ Accordingly, following the Fourier transformation of the signal amplitude function u(x,t) set forth in equation 61, the diffusion equation 1 can be rewritten as follows:

$$\nabla^2 v(x, x_0, k) - \left[\frac{ik}{D(x)} + \frac{a(x)}{D(x)}\right] v(x, x_0, k) = -\frac{\delta(x - x_0)}{D(x_0)} \quad (62)$$

Although equation 62 will now be solved for the general case of signals introduced at a plurality of locations $x_0$ relative to the host medium which have the same frequency k, the signal source of this embodiment can, alternatively, introduce DC signals such that the frequency k can be set equal to 0. Referring to equation 62, the signal processor 20 can define the function q(x,k) as follows:

$$q(x, k) = -\left[\frac{ik}{D(x)} - \frac{a(x)}{D(x)}\right] \quad (63)$$

As a result, equation 62 can be rewritten as:

$$\nabla^2 v(x, x_0) - q(x) v(x, x_0) = -\frac{\delta(x - x_0)}{D(x_0)} \quad (64)$$

As a matter of convenience, any dependence of equation 64 as well as the subsequent equations in Sections E and F upon frequency k is omitted since the signals introduced into the host medium have only a single frequency.

Since the complex valued function q(x) includes both signal propagation properties of the diffusion equation, namely, the diffusion coefficient D(x) and the absorption coefficient a(x), the detection method and apparatus 10 of this embodiment of the present invention can simultaneously determine both signal propagation properties, i.e., D(x) and a(x), by solving for the function q(x). As a result, the detection method and apparatus 10 of this embodiment can simultaneously determine both signal propagation properties, D(x) and a(x), even if neither signal propagation property is predetermined. As a result, the detection method and apparatus of this embodiment permits both signal propagation properties to vary or be perturbed, such as due to changes in the host medium or abnormalities in the host medium.

With reference to FIG. 7, the detectors 14 are located along all of $\partial\Omega$ or along at least a portion of $\Gamma_1$ of the boundary $\partial\Omega$ and the signal source(s) 12 are located along at locations $x_0$ along all or at least a portion of $\Gamma_2$. Although not shown, $\Gamma_2$, along which the source(s) are located, may be offset and below $\Omega$. While $\Gamma_2$ is shown as a straight line, $\Gamma_2$ will more generally be represented by a curve. In this more general embodiment, differentiation will be along the curve in the sense of a directional derivative with respect to source position. Accordingly, each detector 14 will detect a corresponding signal after the signal has propagated through at least a portion of the host medium. As a result, each detector at a location x can generate a function $\phi(x,x_0)$ which forms a boundary condition for the above-described diffusion equation. As described above, if the detectors are located about the entire boundary of the host medium, the detection scheme is termed a complete detection scheme. However, if detectors are positioned at only a portion of the host medium, the detection scheme is termed an incomplete detection scheme. Nevertheless, the various embodiments of the detection method and apparatus 10 of the present invention can be implemented as either a complete or incomplete detection scheme.

In order to determine the function q(x) inside the host medium and, therefore, determine the diffusion coefficient D(x) and the absorption coefficient a(x) within the host medium, the function q(x,k) is defined as $q(x)=q_0(x)+h(x)$ wherein $q_0(x)$ is an approximation of the function q(x) and wherein the perturbation function h(x) is the difference between the actual function q(x) and the approximate function $q_0(x)$ due to perturbations introduced by abnormalities within the host medium and/or changes in the host medium. In addition, for a reference medium having the signal propagation properties defined by the approximation function $q_0(x)$, the signal processor can construct the function $v_0(x,x_0)$ based upon equation 64 as follows:

$$\nabla^2 v_0(x, x_0) - q_0(x) v_0(x, x_0) = -\frac{\delta(x - x_0)}{D(x_0)} \quad (65)$$

wherein $v_0(x,x_0)=0$ on the boundary $\partial\Omega_1$ of the larger medium $\Omega_1$, and the value of the diffusion coefficient D(x) is typically known at $x_0$. Likewise the perturbed function $v(x,x_0)=0$ on the boundary of the host medium.

In a first advantageous embodiment, the signal processor 20 constructs two different forms of the relative difference, i.e., $[v(x,x_0)/v_0(x,x_0)]-1$, instead of a single form of the relative difference as described above, since the initial conditions of the function $v(x,x_0)$ are not known.

In particular, the signal processor 20 of this advantageous embodiment constructs a first difference function as follows:

$$\overline{H}(x, x_0) = \frac{v(x, x_0)}{v_0(x, x_0^{(1)})} - 1 \quad (66)$$

wherein the signal source 12 is located at many positions along $\Gamma_2$, all of which are near $x_0^{(1)}$, and one of which is the fixed position $x_0^{(1)}$. The signal processor then obtains a differential equation and boundary conditions for the derivative $$\frac{\partial \overline{H}(x, x_0)}{\partial x_0}$$

which does not include the perturbation function h(x). In a similar manner to that described above for the time dependent case and as will be described in more detail below. By solving this differential equation, the signal processor determines the function $$\frac{\partial \overline{H}(x, x_0)}{\partial x_0}$$

for all points within the host medium and for all positions of the signal source along a portion of the boundary.

The signal processor 20 of this advantageous embodiment also constructs a second difference function as follows:

$$H(x, x_0) = \frac{v(x, x_0)}{v_0(x, x_0)} - 1 \quad (67)$$

wherein the source position $x_0$ in the numerator and denominator is the same, and again varies along $\Gamma_2$. The signal processor again constructs a partial differential equation for the derivative $$\frac{\partial H(x, x_0)}{\partial x_0}.$$

By comparing functions $$\frac{\partial \overline{H}(x, x_0)}{\partial x_0}$$

and $$\frac{\partial H(x, x_0)}{\partial x_0},$$

the signal processor can construct a partial differential equation for the function $H(x,x_0)$, rather than for the derivative of $H(x,x_0)$. The signal processor then determines the solution of $H(x,x_0)$ and, in turn, the perturbation function $h(x)$.

In particular, the signal source 12 is initially positioned at a source position $x_0^{(1)}$. By setting $\overline{v_0} = v_0(x,x_0^{(1)})$, equation 66 can be rewritten as:

$$\overline{H}(x, x_0) = \frac{v(x, x_0)}{\overline{v_0}} - 1 \tag{68}$$

By assuming that the source position $x_0$ varies within a range including and quite near to $x_0^{(1)}$, the function $v_0(x,x_0^{(1)})$ is close to the function $v_0(x,x_0)$ for all positions of $x_0$ within this range.

The signal processor 20 then substitutes $q_0(x)+h(x)$ for $q(x)$, and linearizes equation 68 for $\overline{H}(x,x_0)$, as follows:

$$\nabla^2 \overline{H}(x, x_0) + 2\frac{\nabla \overline{v_0}}{\overline{v_0}} \nabla \overline{H}(x, x_0) - h(x) = 0 \tag{69}$$

$$\text{wherein } \overline{H}(x, x_0)|_{\Gamma_1} = \frac{\varphi(x, x_0)}{\overline{v_0}} - 1$$

wherein the function $\phi(x,x_0) = v(x,x_0)|_{x \in \Gamma_1}$ is the complex amplitude of the signal being measured by the detectors 14.

The signal processor 20 can then reformulate equation 69 and eliminate the unknown perturbation function $h(x)$ by differentiating equation 69 by $x_0$. By then substituting $p(x,x_0)$ for the derivative of $\overline{H}(x,x_0)$ with respect to the source position xo it follows that:

$$\nabla^2 p(x, x_0) + 2\frac{\nabla \overline{v_0}}{\overline{v_0}} \nabla p(x, x_0) = 0 \tag{70}$$

wherein $$p(x, x_0)|_{\Gamma_1} = \frac{1}{\overline{v_0}} \cdot \frac{\partial \varphi(x, x_0)}{\partial x_0}$$

As described below, for any signal source position $x_0$, the signal processor 20 of this advantageous embodiment can then solve the single elliptic partial differential equation set forth as equation 70 for $p(x,x_0)$, such as by the finite element or the finite difference method.

In the embodiment in which detectors 14 are disposed about the entire boundary, i.e., $\Gamma_1 = \partial \Omega$, equation 70 is a standard boundary value problem for the single elliptic partial differential equation. By solving equation 70 for several source positions $x_0$, the signal processor 20 can determine respective values for the derivative $p(x,x_0) = \overline{H}_{x_0}(x,x_0)$ of the function $\overline{H}(x,x_0,k)$ with respect to the source position $x_0$.

In contrast, in instances in which the detectors 14 are only disposed along a portion of the boundary $\Gamma_1$, the signal processor can again determine the function $p(x,x_0)$ based on the following standard boundary value problem:

$$\nabla^2 p(x, x_0) + 2\frac{\nabla \overline{v_0}}{\overline{v_0}} \nabla p(x, x_0) = 0 \tag{71}$$

$$p(x, x_0)|_{\Gamma} = \begin{cases} \frac{1}{\overline{v_0}} \frac{\partial \varphi(x, x_0)}{\partial x_0} & \text{if } x \in \Gamma_1 \\ 0, \text{ if } x \in \partial \Omega & x \notin \Gamma_1 \end{cases}$$

As described above with regards to equation 67, the function $v_0(x,x_0)$ can allow all signal sources 12 to vary in position $x_0$, without focusing on one source position $x_0^{(1)}$. As a result, the function $H(x,x_0)$ constructed as follows:

$$H(x, x_0) = \frac{v(x, x_0)}{v_0(x, x_0)} - 1 \tag{72}$$

In the same fashion as described above, the signal processor 20 can linearize equation 64 as follows:

$$\nabla^2 H(x, x_0) + 2\frac{\nabla v_0(x, x_0)}{v_0(x, x_0)} \nabla H(x, x_0) - h(x) = 0 \tag{73}$$

wherein $$H(x, x_0)|_{\Gamma_1} = \frac{\varphi(x, x_0)}{v_0(x, x_0)} - 1$$

After setting $$s(x, x_0) = \frac{\partial H(x, x_0)}{\partial x_0},$$

the signal processor 20 eliminates the unknown term $h(x)$ by differentiating equation 73 with respect to $x_0$ to obtain:

$$\nabla^2 s(x, x_0) + 2\frac{\partial}{\partial x_0}\left(\frac{\nabla v_0(x, x_0)}{v_0(x, x_0)}\right) \nabla H(x, x_0) + \tag{74}$$

$$2\frac{\nabla v_0(x, x_0)}{v_0(x, x_0)} \nabla s(x, x_0) = 0$$

wherein $$s(x, x_0)|_{\Gamma_1} = \frac{\partial}{\partial x_0}\left(\frac{\varphi(x, x_0)}{v_0(x, x_0)} - 1\right)$$

The detection method and apparatus 10 of this embodiment obtains a partial differential equation for $H(x,x_0)$, instead of a derivative of $H(x,x_0)$, which avoids having to use any initial conditions for $H(x,x_0)$ once $p(x,x_0)$ is determined. As a result of equation 73, an approximation of the perturbation function $h(x)$ can be immediately determined from the function $H(x,x_0)$.

Based on the above described relationships:

$$s(x, x_0) = \frac{\partial}{\partial x_0} H(x, x_0) = \frac{\partial}{\partial x_0}\left(\frac{v(x, x_0)}{v_0(x, x_0)} - 1\right) = \frac{1}{v_0(x, x_0)} \cdot v_{x_0}(x, x_0) - \frac{\partial v_0(x, x_0)}{\partial x_0} \cdot \frac{1}{v_0(x, x_0)} \cdot \frac{v(x, x_0)}{v_0(x, x_0)} \quad (75)$$

In addition, the function $p(x,x_0)$ can be determined to provide a solution to one of the boundary value equations set forth in equations 70 or 71. It follows from equation 68 that:

$$p(x, x_0) = v_{x_0}(x,, x_0) \cdot \frac{1}{\overline{v}_0} \quad (76)$$

so that $v_{x_0}(x,x_0) = p(x,x_0)\overline{v}_0$. By substituting for $V_{x_0}(x,x_0)$ in equation 75, the function $s(x,x_0)$ can be rewritten as:

$$s(x, x_0) = p(x, x_0)\frac{\overline{v}_0}{v_0(x, x_0)} - \frac{\partial v_0(x, x_0)}{\partial x_0} \cdot \frac{1}{v_0(x, x_0)}(H(x, x_0) + 1) \quad (77)$$

since $$\frac{v(x, x_0)}{v_0(x, x_0)} = H(x, x_0) + 1.$$

In addition, the signal processor 20 can construct the function $f(x,x_0)$ as follows:

$$f(x, x_o) = s(x, x_o) - p(x, x_o)\frac{\overline{v}_o}{v_o(x, x_o)} + \frac{1}{v_o(x, x_o)}\frac{\partial v_o(x, x_o)}{\partial x_o} \quad (78)$$

As a result of equation 77, equation 78 can then be rewritten as:

$$\frac{-1}{v_o(x, x_o)}\frac{\partial v_o(x, x_o)}{\partial x_0}H(x, x_o) = f(x, x_o) \quad (79)$$

Equations 78 and 79 therefore imply that if $$\frac{\partial v_o(x, x_o)}{\partial x_o} = 0,$$

then $f(x,x_0)=0$. In order to solve for the function $H(x,x_0)$, the detection method and apparatus 10 of this embodiment preferably solves for $f(x,x_0)$, since $H(x,x_0)$ is related to $f(x,x_0)$ as described by equation 79.

By rearranging the terms of equation 78, the 10 signal processor 20 can construct the following equation:

$$s(x, x_o) = f(x, x_o) + p(x, x_o)\frac{\overline{v}_o}{v_o(x, x_o)} - \frac{1}{v_o(x, x_o)}\frac{\partial v_o(x, x_o)}{\partial x_o} \quad (80)$$

By substituting equation 80 into equation 74, the following boundary value problem for $f(x,x_0)$ is constructed:

$$\nabla^2 f(x, x_o) - 2\frac{\partial}{\partial x_o}\left(\frac{\nabla v_o(x, x_o)}{v_o(x, x_o)}\right)\nabla\left[f(x, x_o)\frac{v_o(x, x_o)}{x_{ox_o}(x, x_o)}\right] + \quad (81)$$

-continued
$$2\frac{\nabla v_o(x, x_o)}{v_o(x, x_o)}\nabla f(x, x_o) = -g(x, x_o)$$

wherein $$f(x, x_o)|_{\Gamma_1} = s(x, x_o) - p(x, x_o)\frac{\overline{v}_o}{v(x, x_o)} + \frac{1}{v_o(x, x_o)}\frac{\partial v_o(x, x_o)}{\partial x_o}$$

and wherein the function $g(x,x_0)$ can be expressed in terms of known functions by first constructing the function $r(x,x_0)$ as follows:

$$r(x, x_0) = p(x, x_0)\frac{\overline{v}_0}{v_0(x, x_0)} - \frac{1}{v_0(x, x_0)}\frac{\partial v_0(x, x_0)}{\partial x_0} \quad (82)$$

As a result of equations 81 and 82, the function $g(x,x_0)$ can be expressed as:

$$g(x, x_o) = \nabla^2 r(x, x_o) + 2\frac{\nabla v_o(x, x_o)}{v_o(x, x_o)}\nabla r(x, x_o) \quad (83)$$

The signal processor 20 can then solve the elliptic partial differential equation set forth in equation 81 for $f(x,x_0)$ by a direct application of the finite element or the finite difference method. Based on the solution of the partial differential equation, the signal processor 20 can recover $H(x,x_0)$ from equation 79 and, in turn, can recover an approximation of the perturbation function $h(x)$ from equation 73. By recovering an approximation of the perturbation function which is based, at least in part, upon the signal propagation properties, i.e., both the diffusion coefficient $D(x)$ and the absorption coefficient $a(x)$, of the abnormalities through equation 63 wherein $q(x)=q_0(x)+h(x)$, abnormalities within the host medium can be detected.

Two additional embodiments have been developed in instances in which the signals of a single frequency are introduced into the host medium from a variety of positions along $\Gamma_2$. The first approach begins by recognizing that:

$$v(x,x_0)=v^*(x_0,x) \quad (84)$$

wherein the superscript "*" means complex conjugation. As described above and as shown in FIG. 7, the sources 12 and detectors 14 are located along at least a portion of $\Gamma_1$ which is on or somewhat removed from, i.e., below, the boundary $\partial\Omega$ of the medium $\Omega$ of interest. As also described above, the host medium $\Omega$ is a smaller domain than $\Omega_1$, i.e., $\Omega \subset \Omega_1$. As a result, $$\lim_{x_o \to \partial\Omega_1} v(x, x_o) = \lim_{x_o \to \partial\Omega_1} v^*(x_o, x) = 0 \quad (85)$$

By extending the arc $\Gamma_1$ to the boundary $\partial\Omega$, of $\Omega_1$ as shown in dashed lines in FIG. 7, another arc $\Gamma_2$ is obtained. For clarity, the arc $\Gamma_2$ can be assumed to be part of a straight line, that is, $\Gamma_2=\{0 \leq x_1 \leq L, x_2=0, x_3=0\}$, wherein without loss of generality the line begins at (0,0,0). However, both $\Gamma_1$ and $\Gamma_2$ can have other shapes without departing from the spirit and scope of the present invention.

In addition, it is known that:

$$H(x, x_o) = \frac{v(x, x_o)}{v_o(x, x_o)} - 1 \tag{86}$$

$$p(x, x_o) = \frac{\partial H(x, x_o)}{\partial x_o} = \frac{v_{x_o}(x, x_o)}{v_o(x, x_o)} - \frac{v(x, x_o)}{v_o^2(x, x_o)} \frac{\partial v_0(x, x_0)}{\partial x_0} \tag{87}$$

Equation 85 therefore implies that for $x_0 = (x_1^0, 0, 0) \in \Gamma_2$:

$$H(x,x_0) = \int_0^{x1^0} p(x,(z,0,0))dz + C(x) - 1 \tag{88}$$

wherein $$C(x) = \lim_{x_0 \to (0,0,0) \in \partial \Omega_1} \frac{v(x, x_o)}{v_o(x, x_o)} \tag{89}$$

Typically, $C(x)$ is assumed to be one plus a small perturbation which can be determined by an iterative approach. This assumption means that if a source 12 approaches the boundary then both the unperturbed and perturbed solutions are assumed to be equal at any observation point x inside the medium.

The linearized equation for the function $H(x,x_0)$ is:

$$\nabla^2 H(x, x_o) + 2 \frac{\nabla v_o(x, x_o)}{v_o(x, x_o)} \nabla H(x, x_o) - h(x) = 0 \tag{90}$$

Hence, equation 88 implies that the equation for the function $p(x,x_0)$ is:

$$\nabla_x^2 p(x, x_o) + 2 \frac{\partial}{\partial x_o} \left( \frac{\nabla_x v_o(x, x_o)}{v_o(x, x_o)} \int_0^{x_1^2} \nabla_x p(x, (z, 0, 0)) dz \right) = 0 \tag{91}$$

Equation 91 can then be solved in a fashion similar to that of the time dependent case. Namely, for $x_1^o \in (0,L)$, $x_0 \in \Gamma_2$ and $x \in \Omega$, the function $p(x,x_0)$ has the following expansion:

$$p(x, (x_1^0, 0, 0)) \approx p_n(x, (x_1^0, 0, 0)) = \sum_{k=1}^{N} a_k(x_1^0) Q_k(x) \tag{92}$$

wherein functions $\{a_k(x_1^0)\}_{k=1}^{\infty}$ form an orthonormal basis in the space $L_2(a,b)$ and are analytic on the interval $(0,L)$. In addition, functions $Q_k(x)$ are generalized Fourier coefficients of the function $p_N(x,x_0)$ as follows:

$$Q_k(x) = \int_a^b p_N(x_1^o, 0, 0) a_k(x_1^o) dx_1^o \tag{93}$$

This embodiment of the detection method and apparatus 10 then obtains a coupled system of elliptic partial differential equations for the functions $Q_k(x)$ in a manner similar to the time dependent case. The coupled system of elliptic partial differential equations can then be solved in a manner similar to that described in the time dependent case. Thereafter, an approximation of the perturbation function can be obtained as described above, such that abnormalities within the host medium can be detected.

Alternatively, a second advantageous embodiment was developed for instances in which signals of a single frequency are introduced into the host medium from a variety of positions close to an initially fixed source position $x_0^{(1)}$. By letting $\overline{V}_0 = V_0(x, x_0^{(1)})$ be the solution of equation 65 with $x_0 = x_0^{(1)}$, the function $\overline{H}(x,x_0)$ can be defined as follows:

$$\overline{H}(x, x_o) = \frac{v(x, x_o)}{\overline{v}_o} - 1 \tag{94}$$

By assuming that $x_0$ varies, but remains quite near $x_0^{(1)}$, the function $v_0(x,x_0)$ is close to the function $v_0(x,x_0)$ for all positions of $x_0$.

By fixing $x_0^{(1)}$, it can be determined (based on equation 85) that:

$$\lim_{x_o \to (0,0,0) \in \partial \Omega_1} \frac{v(x, x_o)}{\overline{v}_o(x, x_0^{(1)})} = 0 \tag{95}$$

The linearized equations for the function $\overline{H}(x,x_0,k)$ in equation 93 are therefore as follows:

$$\nabla^2 \overline{H}(x, x_o) + 2 \frac{\nabla \overline{v}_o(x, x_o)}{\overline{v}_o(x, x_o)} \nabla \overline{H}(x, x_o) - h(x) = 0 \tag{96}$$

By letting $p(x,x_0) = \overline{H}_{x_o}(x,x_0)$ be the derivative of $\overline{H}(x,x_0)$ with respect to the source position, it is determined that:

$$\nabla^2 p(x, x_o) + 2 \frac{\nabla \overline{v}_o(x, x_o)}{\overline{v}_o(x, x_o)} \nabla p(x, x_o) = 0 \tag{97}$$

$$\overline{H}(x,x_0) = \int_0^{x_1^0} p(x,(z, 0, 0))dz - 1 \tag{98}$$

Thus, a single elliptic partial differential equation of the second order (equation 97) is obtained for the function $p(x,x_0)$. This equation can then be solved by the finite element method, as described above. Once equation 97 has been solved, the function $\overline{H}(x,x_0)$ can be obtained by integration. Thereafter, an approximation of the perturbation function $h(x)$ can be obtained in a manner similar to the time dependent case.

F. Source Position Dependent Signal Propagation Modeled by the Wave Equation

In this embodiment in which the signal source 12 introduces signals which vary according to the source location, the propagation of the signal through the host medium can also be described by the following wave equation:

$$\nabla^2 v(x, x_o) + \frac{1}{c^2(x)}[k^2 + ikb(x) - a(x)]v(x, x_o) = \frac{-\delta(x - x_o)}{c^2(x_o)} \tag{99}$$

As will be apparent, the main difference between equation 99 and diffusion equation 62 is the presence of the term $k^2$.

As described above in conjunction with a diffusion equation, the function $q(x,k)$ can be constructed as follows:

$$q(x, k) = \frac{-1}{c^2(x)}[k^2 + ikb(x) - a(x)] \tag{100}$$

such that equation 99 can be rewritten as:

$$\nabla^2 v(x, x_o) - q(x, k)v(x, x_o) = \frac{-\delta(x - x_o)}{c^2(x_o)} \tag{101}$$

The detection method and apparatus 10 of this embodiment can then solve wave equation 101 in a like manner to that described above in conjunction with diffusion equation 64. Accordingly, if the function $c(x)$ is known, the solution of equation 101 will simultaneously determine both a(x) and b(x). As a result, the detection method and apparatus of this embodiment can also recover an approximation of the perturbation function h(x) so as to detect abnormalities within the host medium since the perturbation function h(x) is based, at least in part, upon the signal propagation properties of the abnormalities, i.e., a(x) and b(x).

G. Frequency Dependent Signal Propagation Modeled by the Diffusion Equation

In yet another alternative embodiment, the signal source 12 is in a fixed position, but introduces signals of different frequencies, including different modulation frequencies in one embodiment, into the host medium. As a result, the detectors 14 of this embodiment will detect the signals corresponding to each frequency.

G1. Option 1

In order to detect abnormalities within the host medium and to determine the signal propagation properties of the detected abnormalities, the signals detected by the detectors corresponding to the input signals of each frequency could be subjected to an inverse Fourier transform with respect to frequency in order to transform the detected signals to the time domain. The detection method and apparatus 10 of this embodiment can then proceed as described above in conjunction with a signal source which provides time dependent signals. This method is especially useful in embodiments in which signals of many frequencies are detected. As described below, the detection method and apparatus of the embodiment which takes an inverse Fourier transform of the detected signals achieves results in the instances in which the signal source provides signals of only a few frequencies.

For example, if the function $\phi(x,k)$ represents the complex amplitude of the detected signals of frequency k on the boundary of the host medium and if the function $\phi(x,t)$ represents the complex signal amplitude of the detected signals at a point x on the boundary of the host medium at a time t, it follows that the function $\phi(x,t)$ and $\phi(x,k)$ are related as follows:

$$\phi(x,k) = \int_0^\infty \phi(x,t) e^{ikt} dt \quad (102)$$

If the function $\phi(x,k)$ was known for all positive frequencies, i.e., $0 < k < \infty$, the signal processor 20 could obtain the function $\phi(x,t)$ using an inverse Fourier transform as follows:

$$\phi(x,t) = \frac{1}{2\pi} \int_{-\infty}^\infty \tilde{\phi}(x,k) e^{-ikt} dk = \quad (103)$$

$$\frac{1}{2\pi} \int_0^\infty \tilde{\phi}(x,k) e^{-ikt} dk + \frac{1}{2\pi} \int_0^\infty \tilde{\phi}^*(x,k) e^{ikt} dk$$

wherein the superscript "*" denotes the complex conjugation of the respective function.

However, since the function $\phi(x,k)$ is given only for a discrete set of points $k_j$ wherein $0 \leq k_j \leq K$, the signal processor 20 can approximate the integrals in equation 103 with discrete sums. For example, one discrete sum is as follows:

$$\phi(x,t) = \frac{1}{4\pi} \sum_{j=1}^{s-1} \left[ \tilde{\phi}(x,k_j) e^{-ik_j t} + \tilde{\phi}(x,k_{j+1}) e^{-ik_{j+1} t} + \quad (104) \right.$$

$$\left. \tilde{\phi}^*(x,k_j) e^{ik_j t} + \tilde{\phi}^*(x,k_{j+1}) e^{ik_{j+1} t} \right] \Delta k_j$$

wherein $\Delta k_j = k_{j+1} - k_j$. It should be apparent, however, that other versions of the approximations of the Fourier integral by discrete sums can also be employed without departing from the spirit and scope of the present invention.

Based on equation 103, it is apparent that as the upper frequency K becomes larger and the maximum difference $(\Delta k_j)_{max}$ between $k_{j+1}$ and $k_j$ becomes less, the function $\phi(x,t)$ is represented more accurately by equation 104. As will therefore be apparent to one skilled in the art, the limitations on the upper frequency K and the maximum difference $(\Delta k_j)_{max}$ between $k_{j+1}$ and $k_j$ are a matter of design choice within the limitations of the signal processor 20, and should be individually selected for each specific application in order to insure that the function $\phi(x,t)$ is represented by equation 104 with sufficient accuracy to meet the constraints of the particular application.

G2. Option 2

In instances in which the function $\phi(x,t)$ is not accurately represented by equation 104, such as in instances in which the signal source 12 provides either signals of many frequencies on a limited interval or signals having only a few frequencies, the detection method and apparatus 10 of the present invention can detect abnormalities within the host medium by determining an approximation of the perturbation function according to another advantageous technique. In this embodiment, the function v(x,k) is a solution of equation 62. For a host medium having an absorption coefficient a(x) which can be defined, as described above, as $a(x) = a_0(x) + h(x)$, the function $v_0(x,t)$ is also the solution of equation 62 with the function a(x) set equal to $a_0(x)$. As a result, the signal processor 20 can construct the following relationship:

$$\frac{v(x,k)}{v_0(x,k)} = 1 + H(x,k) \quad (105)$$

wherein $$\lim_{k \to \infty} H(x,k) = 0.$$

Furthermore, the following integral converges as shown:

$$\int_0^\infty \left[ |H(x,k)|^2 + \left| \frac{\partial H}{\partial k}(x,k) \right|^2 \right] dk < \infty \quad (106)$$

By substituting $v(x,k) = v_0(x,k)(H(x,k)+1)$ into equation 62 and linearizing with respect to h(x), the signal processor 20 can obtain the following equation:

$$\nabla^2 H(x,k) + 2 \frac{\nabla v_0(x,k)}{v_0(x,k)} \nabla H(x,k) - \frac{h(x)}{D(x)} = 0 \quad (107)$$

By setting $$p(x,k) = \frac{\partial H}{\partial k}(x,k),$$

equations 105 and 106 and $$\lim_{k \to \infty} H(x,k) = 0$$

imply:

$$H(x,k) = -\int_k^\infty p(x,z) dz \quad (108)$$

As described above, the detection method and apparatus 10 of this embodiment and, more particularly, the eliminating means 24 of the signal processor 20 then eliminates the terms of the differential equation set forth as equation 107 which include the perturbation function h(x). In this instance, the eliminating means differentiates equation 107 with respect to k to obtain:

$$\nabla^2 p(x,k) - 2\frac{\partial}{\partial k}\left[\frac{\nabla v_0(x,k)}{v_0(x,k)}\int_k^\infty \nabla p(x,z)dz\right] = 0 \quad (109)$$

Based upon the signal amplitude $\Psi(x,k)$ and the flux $\Psi(x,k)$ of the signals detected by each detector 14 for each respective frequency, the signal processor 20 can obtain continuous boundary conditions with respect to x for both signal amplitude $\Psi(x,k)$ and flux $\Psi(x,k)$ by interpolating between each of the detectors for signals of each respective frequency. Thereafter, the signal processor can solve equation 109 in the manner described above to detect abnormalities within the host medium and, based upon the recovered approximation of the perturbation function, to determine the signal properties of the detected abnormalities.

In particular, $\{a_n(k)\}_{n=1}^\infty$ represents a set of orthornormal basis function over the interval of frequencies between $K_0$ and $K_1$ such that the functions $a_n(k)$ are analytic for $K_0 \leq k \leq \infty$ as functions of the real variable k and the following inequality is satisfied:

$$\int_{K_0}^\infty [|a_n(k)|^2 + |a_n(k)|^2]dk < \infty \quad (110)$$

The signal processor 20 can reformulate the function p(x,k) as follows:

$$p(x,k) \approx p_N(x,k) = \sum_{n=1}^N a_n(k)Q_n(x), \text{ for } k \in (K_o, \infty) \quad (111)$$

wherein $Q_n(x)$ are generalized Fourier coefficients of the function p(x,k) over the interval $(K_0, K_1)$. Equation 111 can then be rewritten as:

$$Q_n(x) = \int_{K_0}^{K_1} p_N(x,k)a_n^*(k)dk \quad (112)$$

wherein the superscript "*" denotes complex conjugation. As a result of equation 110, the following integral converges:

$$\int_{K_0}^\infty \sum_{n=1}^N a_n(z)Q_n(x)dz < \infty \quad (113)$$

The signal processor 20 then substitutes equation 112 into equation 109 and obtains the boundary value problem of equation 14 by employing the following orthonormality property of functions $a_n(k)$ $$\int_{K_o}^{K_1} a_n(k)a_m^*(k)dk = \begin{cases} 1, \text{ for } m = n \\ 0, \text{ for } m \neq n \end{cases} \quad (114)$$

Based upon the signals detected at each of the detectors, the signal processor 20 can determine the boundary conditions for the functions $Q_n(x)$ and $$\frac{\partial Q_n(x)}{\partial n}$$

as follows:

$$Q_n(x) = \int_{K_0}^{K_1} \phi(x,k)a_n^*(k)dk \quad (115)$$

$$\frac{\partial Q_n(x)}{\partial n} = \int_{K_o}^{K_1} \tilde{\psi}(x,k)a_n^*(k)dk \quad (116)$$

Thereafter, the signal processor 20 determines a solution to equation 14 in a similar fashion to that described above in conjunction with the time dependent data. Based upon this solution and equation 108, the signal processor then recovers an approximation of the perturbation function h(x) representing, at least in part, the signal propagation properties of the abnormalities within the host medium.

G. Frequency Dependent Signal Propagation Modeled by the Wave Equation

In this embodiment in which the signal source 12 introduces signals which vary in frequency k, including modulation frequency, the propagation of the signals through the host medium can also be described by the wave equation set forth as equation 99. As described above in conjunction with the diffusion equation set forth as equation 57, the signal processor 20 of this embodiment can reformulate wave equation 99 as follows:

$$\nabla^2 H(x,k) + \frac{2\nabla v_0(x,k)}{v_0(x,k)}\nabla H(x,k) - \frac{h(x)}{c^2(x)} = 0 \quad (117)$$

Thereafter, the signal processor 20 can solve equation 117 in a like manner to that described above in conjunction with equation 107. Based upon this solution, the signal processor can then recover an approximation of the perturbation function h(x) representing, at least in part, the signal propagation properties, i.e., a(x), b(x) and c(x), of the abnormalities within the host medium.

H. Summary

Accordingly, the detection method and apparatus 10 of the present invention can detect an abnormality within a host medium by accurately approximating an unknown perturbation function that is based, at least in part, upon the signal propagation properties of the abnormality, such as the absorption coefficient of the abnormality. In particular, the detection method and apparatus constructs at least one partial differential equation at least partially based upon the propagation of a regularized signal through at least a portion of a medium which has the same shape as the host medium. The at least one partial differential equation is constructed to be independent of terms which include the unknown perturbation function, such as by eliminating at least one term which includes the unknown perturbation function prior to solving the at least one partial differential equation, thereby reducing the computational time and effort. According to the present invention, however, an approximation of the perturbation function and, in turn, the first signal propagation property of the abnormality upon which the perturbation function is at least partly based can be recovered once the at least one partial differential equation has been solved such that useful information regarding the abnormality can be obtained in an efficient and timely manner.

The computational effort of the detection apparatus and method of the present invention is further reduced in one embodiment by representing the signals detected along at least a portion of the boundary of the host medium with respective generalized Fourier series having generalized Fourier coefficients. By interpolating between the plurality of generalized Fourier coefficients, a continuous function for each respective generalized Fourier coefficient can be created along at least a portion of the boundary such that the at least one partial differential equation can be solved in a manner which conforms to the generalized Fourier series representing the signals detected at respected ones of the plurality of spaced-apart locations along at least a portion of the boundary.

In the drawings and the specification, there has been set forth preferred embodiments of the invention and, although specific terms are employed, the terms are used in a generic and descriptive sense only and not for the purpose of limitation, the scope of the invention being set forth in the following claims.

That which is claimed is:

1. A method of detecting an abnormality within a host medium of a predetermined shape, wherein the abnormality and the host medium have first and second signal propagation properties, respectively, and wherein the method comprises the steps of:

introducing a signal into the host medium, wherein the signal varies with respect to a predetermined signal parameter;

detecting the signal following propagation through at least a portion of the host medium and an abnormality within the host medium;

constructing at least one differential equation at least partially based upon the propagation of a signal which also varies with respect to the predetermined signal parameter through at least a portion of a medium having a shape corresponding to the shape of the host medium, wherein the at least one differential equation is independent of terms which include an unknown perturbation function, and wherein the unknown perturbation function is at least partially based upon the first signal propagation property of the abnormality;

determining a solution of the at least one differential equation which has been constructed to be independent of the unknown perturbation function, wherein said determining step comprises determining the solution based, at least in part, upon the detected signal; and detecting the abnormality based upon the solution of the at least one differential equation, wherein said detecting step comprises a step of recovering an approximation of the unknown perturbation function that is at least partially based upon the first signal propagation property of the abnormality.

2. A method according to claim 1 wherein said constructing step comprises a step of eliminating at least one term which includes the unknown perturbation function.

3. A method according to claim 1 wherein said introducing step comprises introducing a time-dependent signal into the host medium, wherein said detecting step comprises detecting the signal over time following propagation through at least a portion of the host medium, and wherein the predetermined signal parameter is time such that said constructing step comprises constructing at least one differential equation at least partially based upon variations in a signal over time and such that said determining step comprises determining a solution of the at least one differential equation based upon variations in the detected signal over time and space.

4. A method according to claim 1 wherein said introducing step comprises introducing a plurality of signals into the host medium which are at least partially defined by the predetermined signal parameter, wherein the plurality of signals have different respective values for the predetermined signal parameter, and wherein the respective values of the predetermined signal parameter for the plurality of signals are independent of time.

5. A method according to claim 4 wherein said detecting step comprises detecting a plurality of signals corresponding to respective ones of the plurality of signals introduced into the host medium, and wherein said determining step comprises determining a solution of the at least one differential equation based upon variations in the respective values of the predetermined signal parameter of the plurality of detected signals.

6. A method according to claim 5 wherein the predetermined signal parameter is frequency, and wherein said introducing step further comprises introducing a plurality of signals having different respective frequencies into the host medium.

7. A method according to claim 5 wherein said introducing step further comprises introducing a plurality of signals into the host medium from different locations relative to the host medium such that the location from which the respective signals are introduced relative to the host medium is the signal parameter.

8. A method according to claim 1 further comprising the step of approximating the first and second signal propagation properties of the abnormality and the host medium, respectively.

9. A method according to claim 8 further comprising the step of repeating said approximating, determining and abnormality detecting steps following said step of recovering the perturbation function, wherein said step of approximating the first and second signal propagation properties comprises setting the approximate first and second signal propagation properties equal to a sum of the approximate first and second signal propagation properties from a prior iteration of the method and the perturbation function recovered during the prior iteration of the method.

10. A method according to claim 9 further comprising the step of halting said repeating step if the perturbation function recovered during a current iteration of the method is less than a threshold value for locations within the host medium.

11. A method according to claim 1 wherein the host medium defines a boundary, and wherein said detecting step comprises detecting the signals at a plurality of spaced-apart locations along at least a portion of the boundary following propagation of the signals through at least a portion of the host medium.

12. A method according to claim 11 wherein said detecting step further comprises the steps of:

regularizing the detected signals; and representing the regularized signals associated with each of a plurality of the spaced-apart locations by a generalized Fourier series having generalized Fourier coefficients.

13. A method according to claim 12 wherein said representing step further comprises interpolating between the plurality of generalized Fourier coefficients representative of the regularized signals associated with respective ones of the spaced-apart locations to create a continuous function for each respective generalized Fourier coefficient along at least a portion of the boundary.

14. A method according to claim 13 wherein said constructing step comprises constructing a coupled system of one or more differential equations having unknown terms represented by generalized Fourier coefficients, and wherein said determining step comprises determining a solution to the coupled system of one or more differential equations based upon boundary conditions imposed by the continuous function for each respective generalized Fourier coefficient.

15. An apparatus for detecting an abnormality within a host medium of a predetermined shape, wherein the abnormality and the host medium have first and second signal propagation properties, respectively, and wherein the apparatus comprises:
  a signal source for introducing a signal into the host medium, wherein the signal varies with respect to a predetermined signal parameter;
  at least one detector, responsive to said signal source, for detecting the signal following propagation through at least a portion of the host medium and an abnormality within the host medium; and
  a signal processor, responsive to said at least one detector, for processing the detected signal and for detecting the abnormality, wherein said signal processor comprises:
    means for constructing at least one differential equation at least partially based upon the propagation of a signal which also varies with respect to the predetermined signal parameter through at least a portion of a medium having a shape corresponding to the shape of the host medium, wherein the at least one differential equation is independent of terms which include an unknown perturbation function, and wherein the unknown perturbation function is at least partially based upon the first signal propagation property of the abnormality;
    means, responsive to said constructing means, for determining a solution of the at least one differential equation which has been constructed to be independent of the unknown perturbation function and that is at least partially based upon the detected signal; and
    means, responsive to said solution determining means, for detecting the abnormality based upon the solution of the at least one differential equation, wherein said detecting means comprises means for recovering an approximation of the unknown perturbation function that is at least partially based upon the first signal propagation property of the abnormality.

16. An apparatus according to claim 15 wherein said constructing means comprises means for eliminating at least one term which includes the unknown perturbation function.

17. An apparatus according to claim 15 wherein said signal source introduces a time-dependent signal into the host medium, wherein said at least one detector detects the signal over time following propagation through at least a portion of the host medium, and wherein the predetermined signal parameter is time such that said constructing means constructs at least one differential equation at least partially based upon variations in a signal over time and such that said determining means determines a solution of the at least one differential equation based upon variations in the detected signal over time and space.

18. An apparatus according to claim 15 wherein said signal source introduces a plurality of signals into the host medium which are at least partially defined by the predetermined signal parameter, wherein the plurality of signals have different respective values for the predetermined signal parameter, and wherein the respective values of the predetermined signal parameter for the plurality of signals are independent of time.

19. An apparatus according to claim 18 wherein said detector detects a plurality of signals corresponding to respective ones of the plurality of signals introduced into the host medium, and wherein said determining means determines a solution of the at least one differential equation based upon variations in the respective values of the predetermined signal parameter of the plurality of detected signals.

20. An apparatus according to claim 19 wherein the predetermined signal parameter is frequency, and wherein said signal source introduces a plurality of signals having different respective frequencies into the host medium.

21. An apparatus according to claim 19 wherein said signal source introduces a plurality of signals into the host medium from different locations relative to the host medium such that the location from which the respective signals are introduced relative to the host medium is the signal parameter.

22. An apparatus according to claim 21 wherein said signal source is movable relative to the host medium such that said signal source can introduce a plurality of signals into the host medium from different predetermined locations relative to the host medium.

23. An apparatus according to claim 15 wherein the host medium defines a boundary, and wherein said at least one detector detects signals at a plurality of spaced-apart locations along at least a portion of the boundary following propagation of the signals through at least a portion of the host medium.

24. An apparatus according to claim 23 wherein said at least one detector comprises a plurality of detectors positioned at respective ones of the plurality of spaced-apart locations along at least a portion of the boundary.

25. An apparatus according to claim 24 wherein said signal processor further comprises:
  means for regularizing the detected signals; and
  means, responsive to said regularizing means, for representing the regularized signals associated with each detector by a generalized Fourier series having generalized Fourier coefficients.

26. An apparatus according to claim 25 wherein said representing means comprises means for interpolating between the plurality of generalized Fourier coefficients representative of the regularized signals associated with respective ones of said detectors to create a continuous function for each respective generalized Fourier coefficient along at least a portion of the boundary.

27. An apparatus according to claim 26 wherein said constructing means comprises means for constructing a coupled system of one or more differential equations having unknown terms represented by generalized Fourier coefficients, and wherein said determining means determines a solution to the coupled system of one or more differential equations based upon boundary conditions imposed by the continuous function for each respective generalized Fourier coefficient.

28. A method of detecting an abnormality within a host medium of a predetermined shape based upon a signal that has propagated through at least a portion of the host medium, wherein the signal varies with respect to a predetermined signal parameter, wherein the abnormality and the host medium have different signal propagation properties, and wherein the method comprises the steps of:
  analyzing the signal that has propagated through at least a portion of the host medium to determine variations in the signal with respect to the predetermined signal parameter;
  constructing at least one differential equation at least partially based upon the propagation of a signal which also varies with respect to the predetermined signal parameter through at least a portion of a medium having a shape corresponding to the shape of the host medium, wherein the at least one differential equation is independent of terms which include an unknown perturbation function, and wherein the unknown perturbation function is at least partially based upon the signal propagation property of the abnormality;

determining a solution of the at least one differential equation which has been constructed to be independent of the unknown perturbation function, wherein said determining step comprises determining the solution based, at least in part, upon the variations in the signal with respect to the predetermined signal parameter; and detecting the abnormality based upon the solution of the at least one differential equation, wherein said detecting step comprises a step of recovering an approximation of the unknown perturbation function that is at least partially based upon the signal propagation property of the abnormality.

29. A method according to claim 28 wherein said constructing step comprises a step of eliminating at least one term which includes the unknown perturbation function.

30. A method according to claim 28 wherein the predetermined signal parameter is time, wherein said analyzing step comprises analyzing a time-dependent signal which has propagated through at least a portion of the host medium to determine variations in the signal over time, wherein said constructing step comprises constructing at least one differential equation at least partially based upon variations in a signal over time, and wherein said determining step comprises determining a solution of the at least one differential equation based upon variations in the detected signal over time and space.

31. A method according to claim 28 wherein said analyzing step comprises analyzing a plurality of signals that have propagated through the host medium and are at least partially defined by the predetermined signal parameter, wherein the plurality of signals have different respective values for the predetermined signal parameter, and wherein the respective values of the predetermined signal parameter for the plurality of signals are independent of time.

32. A method according to claim 31 wherein said analyzing step comprises analyzing a plurality of signals which have propagated through at least a portion of the host medium and which have different respective values for the predetermined signal parameter, and wherein said determining step comprises determining a solution of the at least one differential equation based upon variations in the respective values of the predetermined signal parameter of the plurality of detected signals.

33. A method according to claim 32 wherein the predetermined signal parameter is selected from the group consisting of frequency of the respective signals and relative location from which the respective signals are introduced into the host medium.

34. A method according to claim 28 wherein the abnormality and the host medium have first and second signal propagation properties, respectively, and wherein the method further comprises the step of approximating the first and second signal propagation properties of the abnormality and the host medium, respectively.

35. A method according to claim 34 further comprising the step of repeating said approximating, determining and abnormality detecting steps following said step of recovering the perturbation function, wherein said step of approximating the first and second signal propagation properties comprises setting the approximate first and second signal propagation properties equal to a sum of the approximate first and second signal propagation properties from a prior iteration of the method and the perturbation function recovered during the prior iteration of the method.

36. A method according to claim 35 further comprising the step of halting said repeating step if the perturbation function recovered during a current iteration of the method is less than a threshold value for locations within the host medium.

37. A method according to claim 28 wherein the host medium defines a boundary, and wherein said analyzing step comprises the steps of:

regularizing signals that have propagated through at least a portion of the host medium to reach a plurality of spaced-apart locations along at least a portion of the boundary; and representing the regularized signals associated with each of the spaced-apart locations by a generalized Fourier series having a generalized Fourier coefficients.

38. A method according to claim 37 wherein said representing step further comprises interpolating between the plurality of generalized Fourier coefficients representative of the regularized signals associated with respective ones of the spaced-apart locations to create a continuous function for each respective generalized Fourier coefficient along at least a portion of the boundary.

39. A method according to claim 38 wherein said constructing step comprises constructing a coupled system of one or more differential equations having unknown terms represented by generalized Fourier coefficients, and wherein said determining step comprises determining a solution to the coupled system of one or more differential equations based upon boundary conditions imposed by the continuous function for each respective generalized Fourier coefficient.

40. A signal processor for detecting an abnormality within a host medium of a predetermined shape based upon a signal that has propagated through at least a portion of the host medium, wherein the signal varies with respect to a predetermined signal parameter, wherein the abnormality and the host medium have different signal propagation properties, and wherein the signal processor comprises:

means for analyzing the signal that has propagated through at least a portion of the host medium to determine variations in the signal with respect to the predetermined signal parameter;

means, responsive to said analyzing means, for constructing at least one differential equation at least partially based upon the propagation of a signal which also varies with respect to the predetermined signal parameter through at least a portion of a medium having a shape corresponding to the shape of the host medium, wherein the at least one differential equation is independent of terms which include an unknown perturbation function, and wherein the unknown perturbation function is at least partially based upon the signal propagation property of the abnormality;

means, responsive to said constructing means, for determining a solution of the at least one differential equation which has been constructed to be independent of the unknown perturbation function and that is at least partially based upon the variations in the signal with respect to the predetermined signal parameter; and means, responsive to said solution determining means, for detecting the abnormality based upon the solution of the at least one differential equation, wherein said detecting means comprises means for recovering an approximation of the unknown perturbation function that is at least partially based upon the signal propagation property of the abnormality.

41. A signal processor according to claim 40 wherein said constructing means comprises means for eliminating at least one term which includes the perturbation function.

42. A signal processor according to claim 40 wherein the predetermined signal parameter is time, wherein said analyzing means analyzes a time-dependent signal which has propagated through at least a portion of the host medium to determine variations in the signal over time, wherein said constructing means constructs at least one differential equation at least partially based upon variations in a signal over time, and wherein said determining means determines a solution of the at least one differential equation based upon variations in the detected signal over time and space.

43. A signal processor according to claim 40 wherein said analyzing means analyzes a plurality of signals that have propagated through the host medium and are at least partially defined by the predetermined signal parameter, wherein the plurality of signals have different respective values for the predetermined signal parameter, and wherein the respective values of the predetermined signal parameter for the plurality of signals are independent of time.

44. A signal processor according to claim 43 wherein said analyzing means analyzes a plurality of signals which have propagated through at least a portion of the host medium and which have different respective values for the predetermined signal parameter, and wherein said determining means determines a solution of the at least one differential equation based upon variations in the respective values of the predetermined signal parameter of the plurality of detected signals.

45. A signal processor according to claim 44 wherein the predetermined signal parameter is selected from the group consisting of frequency of the respective signals and relative location from which the respective signals are introduced into the host medium.

46. A signal processor according to claim 40 wherein the host medium defines a boundary, wherein said analyzing means further comprises:
   means for regularizing signals that have propagated through at least a portion of the host medium to reach a plurality of spaced-apart locations along at least a portion of the boundary; and
   means, responsive to said regularizing means, for representing the regularized signals associated with each of the spaced-apart locations by a generalized Fourier series having generalized Fourier coefficients.

47. A signal processor according to claim 46 wherein said representing means comprises means for interpolating between the plurality of generalized Fourier coefficients representative of the regularized signals associated with respective ones of the spaced-apart locations to create a continuous function for each respective generalized Fourier coefficient along at least a portion of the boundary, wherein said constructing means comprises means for constructing a coupled system of one or more differential equations having unknown terms represented by generalized Fourier coefficients, and wherein said determining means determines a solution to a coupled system of one or more differential equations based upon boundary conditions imposed by the continuous function for each respective generalized Fourier coefficient.

48. A method of detecting an abnormality within a host medium of a predetermined shape based upon signals that have propagated through at least a portion of the host medium, wherein the signals vary with respect to a predetermined signal parameter, wherein the abnormality and the host medium have different signal propagation properties, and wherein the method comprises the steps of:
   regularizing the signals that have propagated through at least a portion of the host medium to reach a plurality of spaced-apart locations along at least a portion of a boundary of the host medium;
   representing a derivative of the regularized signals reaching each of the spaced-apart locations by a generalized Fourier series having generalized Fourier coefficients;
   constructing a coupled system of differential equations having unknown terms represented by generalized Fourier coefficients at least partially based upon the propagation of a regularized signal through at least a portion of a medium having a shape corresponding to the shape of the host medium, wherein the regularized signal also varies with respect to the predetermined signal parameter;
   determining a solution of the coupled system of differential equations based upon boundary conditions imposed by the generalized Fourier series representing the regularized signals reaching each of the plurality of spaced-apart locations along the boundary of the host medium; and
   detecting the abnormality based upon the solution of the coupled system of differential equations.

49. A method according to claim 48 wherein said representing step further comprises interpolating between the plurality of generalized Fourier coefficients representative of the derivative of the regularized signals associated with respective ones of the spaced-apart locations to create a continuous function for each respective generalized Fourier coefficient along at least a portion of the boundary.

50. A method according to claim 48 wherein the predetermined signal parameter is selected from the group consisting of time, frequency of the respective signals and relative location from which the respective signals are introduced into the host medium.

51. A signal processor for detecting an abnormality within a host medium of a predetermined shape based upon signals that have propagated through at least a portion of the host medium, wherein the signals vary with respect to a predetermined signal parameter, wherein the abnormality and the host medium have different signal propagation properties, and wherein the signal processor comprises:
   means for regularizing the signals that have propagated through at least a portion of the host medium to reach a plurality of spaced-apart locations along at least a portion of a boundary of the host medium;
   means for representing a derivative of the regularized signals reaching each of the spaced-apart locations by a generalized Fourier series having generalized Fourier coefficients;
   means for constructing a coupled system of differential equations having unknown terms represented by generalized Fourier coefficients at least partially based upon the propagation of a regularized signal through at least a portion of a medium having a shape corresponding to the shape of the host medium, wherein the regularized signal also varies signal with respect to the predetermined signal parameter;
   means, responsive to said analyzing means and said constructing means, for determining a solution of the coupled system of differential equations based upon boundary conditions imposed by the generalized Fourier series representing the regularized signals reaching each of the plurality of spaced-apart locations along the boundary of the host medium; and
   means, responsive to said solution determining means, for detecting the abnormality based upon the solution of the coupled system of differential equations.

52. A signal processor according to claim 51 wherein said representing means further comprises means for interpolating between the plurality of generalized Fourier coefficients representative of the derivative of the regularized signals associated with respective ones of the spaced-apart locations to create a continuous function for each respective generalized Fourier coefficient along at least a portion of the boundary.

53. A signal processor according to claim 51 wherein the predetermined signal parameter is selected from the group consisting of time, frequency of the respective signals and relative location from which the respective signals are introduced into the host medium.

54. A computer program product for detecting an abnormality within a host medium of a predetermined shape based upon a signal that has propagated through at least a portion of the host medium, wherein the signal varies with respect to a predetermined signal parameter, wherein the abnormality and the host medium have different signal propagation properties, and wherein the computer program product comprises a computer-readable storage medium having computer-readable program code means embodied in said medium, said computer-readable program code means comprising:

first computer-readable program code means for analyzing the signal that has propagated through at least a portion of the host medium to determine variations in the signal with respect to the predetermined signal parameter;

second computer-readable program code means, responsive to said first computer-readable program code means, for constructing at least one differential equation at least partially based upon the propagation of a signal which also varies with respect to the predetermined signal parameter through at least a portion of a medium having a shape corresponding to the shape of the host medium, wherein the at least one differential equation is independent of terms which include an unknown perturbation function, and wherein the unknown perturbation function is at least partially based upon the signal propagation property of the abnormality;

third computer-readable program code means, responsive to said second computer-readable program code means, for determining a solution of the at least one differential equation which has been constructed to be independent of the unknown perturbation function and that is at least partially based upon the variations in the signal with respect to the predetermined signal parameter; and fourth computer-readable program code means, responsive to said third computer-readable program code means, for detecting the abnormality based upon the solution of the at least one differential equation, wherein said fourth computer-readable program means comprises computer-readable program code means for recovering an approximation of the unknown perturbation function that is at least partially based upon the signal propagation property of the abnormality.

55. A computer program product according to claim 54 wherein the predetermined signal parameter is time, wherein said first computer-readable program code means analyzes a time-dependent signal which has propagated through at least a portion of the host medium to determine variations in the signal over time, wherein said second computer-readable program code means constructs at least one differential equation at least partially based upon variations in a signal over time, and wherein said third computer-readable program code means determines a solution of the at least one differential equation based upon variations in the detected signal over time and space.

56. A computer program product according to claim 54 wherein said first computer-readable program code means analyzes a plurality of signals that have propagated through the host medium and are at least partially defined by the predetermined signal parameter, wherein the plurality of signals have different respective values for the predetermined signal parameter, and wherein the respective values of the predetermined signal parameter for the plurality of signals are independent of time.

57. A computer program product according to claim 56 wherein said first computer-readable program code means analyzes a plurality of signals which have propagated through at least a portion of the host medium and which have different respective values for the predetermined signal parameter, and wherein said third computer-readable program code means determines a solution of the at least one differential equation based upon variations in the respective values of the predetermined signal parameter of the plurality of detected signals.

58. A computer program product according to claim 57 wherein the predetermined signal parameter is selected from the group consisting of frequency of the respective signals and relative location from which the respective signals are introduced into the host medium.

59. A computer program product according to claim 54 wherein the host medium defines a boundary, and wherein said first computer-readable program code means further comprises:

fifth computer-readable code means for regularizing signals that have propagated through at least a portion of the host medium to reach a plurality of spaced-apart locations along at least a portion of the boundary; and sixth computer-readable program code means, responsive to said fifth computer-readable code means, for representing the regularized signals associated with each of the spaced-apart locations by a generalized Fourier series having generalized Fourier coefficients.

* * * * *

UNITED STATES PATENT AND TRADEMARK OFFICE
CERTIFICATE OF CORRECTION

PATENT NO. : 5,963,658
DATED : October 5, 1999
INVENTOR(S) : Klibanov et al.

It is certified that error appears in the above-identified patent and that said Letters Patent is hereby corrected as shown below:

Title page, item

[56] References Cited, OTHER PUBLICATIONS, page 2, column 1, line 10, "575-296" should read --575-96--; column 2, line 6, "Hyerbolic" should read --Hyperbolic--; line 27, after "Release" insert a comma (,) and a space; line 36, "Antomically" should read --Anatomically--.

Column 27, after line 35, cancel the following:

" $G_1(x,t) = \int_0^t G(x,\tau) d\tau$ $$\bar{u}_0(x, t) = \frac{1}{D_0(x)}\left[u_0(x, t) + a(x)\int_0^t u_0(x, \tau) d\tau\right] \quad (28)$$ "

and insert the following:

$$G_1(x, t) = \int_0^t G(x,\tau) d\tau$$
$$\bar{u}_0(x, t) = \int_0^t \nabla^2 u_0(x,\tau) d\tau \quad (27)$$

Based upon equations 1 and 27, the equation for $\bar{u}_0(x,t)$ can be rewritten as follows:

$$\bar{u}_0(x, t) = \frac{1}{D_0(x)}\left[u_0(x, t) + a(x)\int_0^t u_0(x,\tau) d\tau\right] \quad (28) --.$$

Signed and Sealed this

Twenty-fifth Day of April, 2000

Attest:

Q. TODD DICKINSON

*Attesting Officer*          *Director of Patents and Trademarks*